(12) United States Patent
Chen et al.

(10) Patent No.: US 10,526,649 B2
(45) Date of Patent: Jan. 7, 2020

(54) AUGMENTING IN SITU NUCLEIC ACID SEQUENCING OF EXPANDED BIOLOGICAL SAMPLES WITH IN VITRO SEQUENCE INFORMATION

(71) Applicants: Massachusetts Institute of Technology, Cambridge, MA (US); President and Fellows of Harvard College, Cambridge, MA (US)

(72) Inventors: Fei Chen, Cambridge, MA (US); Shahar Alon, Cambridge, MA (US); Andrew Payne, Cambridge, MA (US); Asmamaw Wassie, Boston, MA (US); Daniel Goodwin, Somerville, MA (US); Edward Stuart Boyden, Chestnut Hill, MA (US); Evan Daugharthy, Cambridge, MA (US); Jonathan Scheiman, New York, NY (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 133 days.

(21) Appl. No.: 15/789,419

(22) Filed: Oct. 20, 2017

(65) Prior Publication Data
US 2018/0119219 A1    May 3, 2018

Related U.S. Application Data

(63) Continuation-in-part of application No. 15/098,968, filed on Apr. 14, 2016, now Pat. No. 10,059,990.

(60) Provisional application No. 62/147,204, filed on Apr. 14, 2015.

(51) Int. Cl.
*C12Q 1/6874* (2018.01)
*C12Q 1/6841* (2018.01)

(52) U.S. Cl.
CPC ......... *C12Q 1/6874* (2013.01); *C12Q 1/6841* (2013.01)

(58) Field of Classification Search
CPC ............................ C12Q 1/6874; C12Q 1/6841
USPC ........................................................ 506/16
See application file for complete search history.

(56) References Cited

U.S. PATENT DOCUMENTS

| 5,952,232 A | 9/1999 | Rothman |
|---|---|---|
| 6,107,081 A | 8/2000 | Feedback et al. |
| 6,271,278 B1 | 8/2001 | Park et al. |
| 6,287,870 B1 | 9/2001 | Wardlaw |
| 2002/0176880 A1 | 11/2002 | Cruise et al. |
| 2003/0120231 A1 | 6/2003 | Wang |
| 2004/0248326 A1 | 12/2004 | Ziaie et al. |
| 2005/0034990 A1 | 2/2005 | Crooks et al. |
| 2005/0090016 A1 | 4/2005 | Rich et al. |
| 2005/0169962 A1 | 8/2005 | Bhatia et al. |
| 2005/0196702 A1 | 9/2005 | Bryant et al. |
| 2006/0000767 A1 | 1/2006 | Trauger |
| 2006/0003356 A1 | 1/2006 | Shaw et al. |
| 2006/0110760 A1 | 5/2006 | Kim et al. |
| 2006/0115146 A1 | 6/2006 | Ogura et al. |
| 2006/0165912 A1 | 7/2006 | Koberstein et al. |
| 2007/0023942 A1 | 2/2007 | Andino et al. |
| 2007/0134902 A1 | 6/2007 | Bertino et al. |
| 2008/0261834 A1 | 10/2008 | Simon |
| 2008/0286360 A1 | 11/2008 | Shoichet et al. |
| 2009/0011141 A1 | 1/2009 | Carter et al. |
| 2009/0011420 A1 | 1/2009 | Barron et al. |
| 2009/0096133 A1 | 4/2009 | Doyle et al. |
| 2009/0191627 A1 | 7/2009 | Fadeev et al. |
| 2009/0241681 A1 | 10/2009 | Machauf |
| 2010/0041128 A1 | 2/2010 | Banes et al. |
| 2010/0055161 A1 | 3/2010 | Ahn |
| 2010/0056445 A1 | 3/2010 | Sharma et al. |
| 2010/0068725 A1 | 3/2010 | Armbrumster et al. |
| 2010/0096334 A1 | 4/2010 | Edmiston |
| 2010/0119755 A1 | 5/2010 | Chung et al. |
| 2011/0070604 A1 | 3/2011 | Gimzewski et al. |
| 2011/0009171 A1 | 4/2011 | Weiss |
| 2011/0087315 A1 | 4/2011 | Richardson-Burns et al. |
| 2011/0091922 A1 | 4/2011 | Krishnan et al. |
| 2011/0291357 A1 | 12/2011 | Boyle |
| 2012/0184670 A1 | 7/2012 | Kobayashi et al. |
| 2012/0220478 A1* | 8/2012 | Shaffer ............... C12Q 1/6886 506/9 |
| 2012/0251527 A1 | 10/2012 | Reiser |

(Continued)

FOREIGN PATENT DOCUMENTS

| JP | 2009191125 | 8/2009 |
|---|---|---|
| JP | 2014005231 | 1/2014 |
| WO | 200008212 | 2/2000 |
| WO | 2012142664 | 10/2012 |
| WO | 2014025392 A1 | 2/2014 |
| WO | 2014152984 | 9/2014 |
| WO | 2015127183 | 8/2015 |
| WO | 2017027367 | 2/2017 |
| WO | 2017027368 | 2/2017 |

OTHER PUBLICATIONS

Lee et al. ( Sciencexpress. Feb. 27, 2014, pp. 1-6) (Year: 2014).*
Nilsson, M., et al., "RNA-Templated DNA Ligation for Transcript Analysis," Nucleic Acids Research, 29(2): pp. (2001). 578-581.
Park, Y., et al., Detection of Hepatitis C Virus RNA Using Ligation-Dependent Polymerase Chain Reaction in Formalin-Fixed, Paraffin-Embedded Liver Tissues, American Journal of Pathology, 149(5): pp. 1485-1491 (1996).

(Continued)

*Primary Examiner* — Karla A Dines
(74) *Attorney, Agent, or Firm* — Elmore Patent Law Group, P.C.; Joseph Zucchero; Carolyn Elmore

(57) ABSTRACT

The invention provides in situ nucleic acid sequencing to be conducted in biological specimens that have been physically expanded. The invention leverages the techniques for expansion microscopy (ExM) to provide new methods for in situ sequencing of nucleic acids in a process referred to herein as "expansion sequencing" (ExSEQ).

21 Claims, 17 Drawing Sheets
(16 of 17 Drawing Sheet(s) Filed in Color)
Specification includes a Sequence Listing.

(56) References Cited

U.S. PATENT DOCUMENTS

| | | |
|---|---|---|
| 2012/0310223 A1 | 12/2012 | Knox et al. |
| 2013/0045503 A1 | 2/2013 | Miyawaki et al. |
| 2013/0203605 A1* | 8/2013 | Shendure ........... C12N 15/1093 506/2 |
| 2014/0087139 A1 | 3/2014 | Rowley et al. |
| 2014/0193651 A1 | 7/2014 | Kharlampieva et al. |
| 2016/0116384 A1 | 4/2016 | Chen et al. |
| 2016/0252528 A1 | 9/2016 | Sangarlingham et al. |
| 2016/0304952 A1 | 10/2016 | Boyden et al. |
| 2016/0305856 A1 | 10/2016 | Boyden et al. |
| 2017/0067096 A1 | 3/2017 | Wassie et al. |
| 2017/0081489 A1 | 3/2017 | Rodriques et al. |
| 2017/0089811 A1 | 3/2017 | Tillberg et al. |

OTHER PUBLICATIONS

Laemmli, U. K. Cleavage of structural proteins during the assembly of the head of bacteriophage T4. Nature 227, 680-685 (1970).
Hunt, et al., High temperature antigen retrieval and loss of nuclear morphology: a comparison of microwave\rand autoclave techniques. J. Clin. Pathol. 49, 767-770 (1996).
Jekel, P. A., Weijer, W. J. & Beintema, J. J. Use of endoproteinase Lys-C from Lysobacter enzymogenes in protein sequence analysis. Anal. Biochem. 134, 347-354 (1983).
Wu, C. C., MacCoss, M. J., Howell, K. E. & Yates, J. R. A method for the comprehensive proteomic analysis of membrane proteins. Nat. Biotechnol. 21, 532-8 (2003).
Sniegowski, J. A., Phail, M. E. & Wachter, R. M. Maturation efficiency, trypsin sensitivity, and optical properties of Arg96, Glu222, and Gly67 variants of green fluorescent protein. Biochem. Biophys. Res. Commun. 332, 657-63 (2005).
Bokman, S. H. & Ward, W. W. Renaturation of Aequorea gree-fluorescent protein. Biochem. Biophys. Res. Commun. 101, 1372-80 (1981).
Seneviratne, U. et al. S-nitrosation of proteins relevant to Alzheimer's disease during early stages of neurodegeneration. Proc. Natl. Acad. Sci. U. S. A. 1521318113—(2016). doi:10.1073/pnas.1521318113.
Huang, B., Jones, S. A., Brandenburg, B. & Zhuang, X. Whole-cell 3D STORM reveals interactions between cellular structures with nanometer-scale resolution. Nat. Methods 5, 1047-1052 (2008).
Rego, E. H. et al. Nonlinear structured-illumination microscopy with a photoswitchable protein reveals cellular structures at 50-nm resolution. Proc. Natl. Acad. Sci. U. S. A. 109, E135-43 (2012).
Bates, M., Huang, B., Dempsey, G. T. & Zhuang, X. Multicolor super-resolution imaging with photo-switchable fluorescent probes. Science 317, 1749-1753 (2007).
Bossi, M. et al. Multicolor far-field fluorescence nanoscopy through isolated detection of distinct molecular species. Nano Lett. 8, 2463-8 (2008).
Livet, J. et al. Transgenic strategies for combinatorial expression of fluorescent proteins in the nervous system. Nature 450, 56-62 (2007).
Schnell, U. Dijk, F. Sjollema, K. A. & Giepmans, B. N. G. Immunolabeling artifacts and the need for live-cell imaging. Nat. Methods 9,152-158 (2012).
Hackstadt, T. Steric hindrance of antibody binding to surface proteins of Coxiella burnetti by phase I lipopolysaccharide. Infect Immun 56, 802-807 (1988).
Jimenez, N. & Post, J. A. A Novel Approach for Intracellular 3D Immuno-Labeling for Electron Tomography. Traffic 13, 926-933 (2012).
Randall, K. J. & Pearse, G. A dual-label technique for the immunohistochemical demonstration of T-lymphocyte subsets in formalin-fixed, paraffin-embedded rat lymphoid tissue. Toxicol. Pathol. 36, 795-804 (2008).
Kakimoto, K., Takekoshi, S., Miyajima, K. & Osamura, R. Y. Hypothesis for the mechanism for heat-induced antigen retrieval occurring on fresh frozen sections without formalin-fixation in immunohistochemistry. J Mol Histol 39, 389-399 (2008).

Wachter, R. M. & James Remington, S. Sensitivity of the yellow variant of green fluorescent protein to halides and nitrate. Curr. Biol. 9, R628-R629 (1999).
Carpenter, A. E. et al. CellProfiler: image analysis software for identifying and quantifying cell phenotypes. Genome Biol. 7, R100 (2006).
Kroon, D.-J. B-spline Grid, Image and Point based Registration. Matlab Cent. at <http://www.mathworks.com/matlabcentral/fileexchange/20057-b-spline-grid--image-and-point-based-registration>.
Lowe, D. G. Distinctive Image Features from Scale-Invariant Keypoints. Int. J. Comput. Vis. 60, 91-110 (2004).
Vedaldi, A. & Fulkerson, B. Vlfeat. in Proc. Int. Conf. Multimed.—MM '10 1469 (ACM Press, 2010). doi:10.1145/1873951.1874249.
English, B. P. & Singer, R. H. A three-camera imaging microscope for high-speed single-molecule tracking and super-resolution imaging in living cells. in SPIE Nanosci. + Eng. (Mohseni, H., Agahi, M. H. & Razeghi, M.) 955008 (International Society for Optics and Photonics, 2015). doi:10.1117/12.2190246.
Edelstein, A., Amodaj, N., Hoover, K., Vale, R. & Stuurman, N. Computer control of microscopes using µManager. Curr. Protoc. Mol. Biol. Chapter 14, Unit14.20 (2010).
Dedecker, P., Duwé, S., Neely, R. K. & Zhang, J. Localizer: fast, accurate, open-source, and modular software package for super-resolution microscopy. J. Biomed. Opt. 17, 126008 (2012).
Mortensen, K. I., Churchman, L. S., Spudich, J. A. & Flyvbjerg, H. Optimized localization analysis for single-molecule tracking and super-resolution microscopy. Nat. Methods 7, 377-81 (2010).
Al, H., Shaner, N. C., Cheng, Z., Tsien, R. Y. & Campbell, R. E. Exploration of new chromophore structures leads to the identification of improved blue fluorescent proteins. Biochemistry 46, 5904-10 (2007).
Subach, O. M., Cranfill, P. J., Davidson, M. W. & Verkhusha, V. V. An Enhanced Monomeric Blue Fluorescent Protein with the High Chemical Stability of the Chromophore. PLoS One 6, e28674 (2011).
Goedhardt, J. et al. Structure-guided evolution of cyan fluorescent proteins towards a quantum yield of 93%. Nat. Commun. 3, 751 (2012).
Markwardt, M. L. et al. An improved cerulean fluorescent protein with enhanced brightness and reduced reversible photoswitching. PLoS One 6, e17896 (2011).
Heim, R., Prasher, D. C. & Tsien, R. Y. Wavelength mutations and posttranslational autoxidation of green fluorescent protein. Proc. Natl. Acad. Sci. U. S. A. 91, 12501-4 (1994).
Heim, R. & Tsien, R. Y. Engineering green fluorescent protein for improved brightness, longer wavelengths and fluorescence resonance energy transfer. Curr. Biol. 6, 178-82 (1996).
Rose, R. C. & Bode, A. M. Ocular ascorbate transport and metabolism. Comp. Biochem. Physiol. A. Comp. Physiol. 100, 273-85 (1991).
Cubitt, A. B., Woollenweber, L. A. & Heim, R. Understanding structure-function relationships in the Aequorea victoria green fluorescent protein. Methods Cell Biol. 58, 19-30 (1999).
Cormack, B. P., Valdivia, R. H. & Falkow, S. FACS-optimized mutants of the green fluorescent protein (GFP). Gene 173, 33-8 (1996).
Lam, A. J. et al. Improving FRET dynamic range with bright green and red fluorescent proteins. Nat. Methods 9, 1005-12 (2012).
Ormo, M. et al. Crystal structure of the Aequorea victoria green fluorescent protein. Science 273, 1392-5 (1996).
Nagai, T. et al. A variant of yellow fluorescent protein with fast and efficient maturation for cell-biological applications. Nat. Biotechnol. 20, 87-90 (2002).
Griesbeck, O., Baird, G. S., Campbell, R. E., Zacharias, D. A. & Tsien, R. Y. Reducing the environmental sensitivity of yellow fluorescent protein. Mechanism and applications. J. Biol. Chem. 276, 29188-94 (2001).
Shaner, N. C. et al. Improving the photostability of bright monomeric orange and red fluorescent proteins. Nat. Methods 5, 545-51 (2008).
Shcherbakova, D. M., Hink, M. A., Joosen, L., Gadella, T. W. J. & Verkhusha, V. V. An orange fluorescent protein with a large Stokes

(56) References Cited

OTHER PUBLICATIONS shift for single-excitation multicolor FCCS and FRET imaging. J. Am. Chem. Soc. 134, 7913-23 (2012).
Shaner, N. C. et al. Improved monomeric red, orange and yellow fluorescent proteins derived from *Discosoma* sp. red fluorescent protein. Nat. Biotechnol. 22, 1567-72 (2004).
Shcherbo, D. et al. Far-red fluorescent tags for protein imaging in living tissues. Biochem. J. 418, 567-74 (2009).
Chu, J. et al. Non-invasive intravital imaging of cellular differentiation with a bright red-excitable fluorescent protein. Nat. Methods 11, 572-8 (2014).
Filonov, G. S. et al. Bright and stable near-infrared fluorescent protein for in vivo imaging. Nat. Biotechnol. 29, 757-61 (2011).
Gurskaya, N. G. et al. Engineering of a monomeric green-to-red photoactivatable fluorescent protein induced by blue light. Nat. Biotechnol. 24, 461-5 (2006).
McKinney, S. A., Murphy, C. S., Hazelwood, K. L., Davidson, M. W. & Looger, L. L. A bright and photostable photoconvertible fluorescent protein. Nat. Methods 6, 131-3 (2009).
Habuchi, S., Tsutsui, H., Kochaniak, A. B., Miyawaki, A. & van Oijen, A. M. mKikGR, a monomeric photoswitchable fluorescent protein. PLoS One 3, e3944 (2008).
Subach F. V, Patterson, G. H., Renz, M., Lippincott-Schwartz, J. & Verkhusha, V. V. Bright monomeric photoactivatable red fluorescent protein for two-color super-resolution sptPALM of live cells. J. Am. Chem. Soc. 132, 6481-91 (2010).
Kaur, et al., Biochemistry 45, pp. 7347-7355 (2006).
Cai, et al., Nat Meth 10, pp. 540-547 (2013).
Zimmerman, et al., Adapting the stretched sample method from tissue profiling to imaging, Proteomics, 8, (2008), p. 3809-3815. (Year: 2008).
Chang, et al., Iterative expansion microscopy, Nature Methods, 14(6), (2017), p. 593-599, and supplemental info (4 pages, 11 pages total) (Year: 2017).
Chen, F., et al., "Expansion Microscopy," Science, vol. 347, No. 6221, p. 543, Jan. 2015.
Chen, F., et al., "Nanoscale Imaging of RNA with Expansion Microscopy," HHS Public Access Author Manuscript, vol. 13(8): pp. 679-684 (Aug. 2016).
Chen, F., et al., "Supplementary Material for Expansion Microscopy," Science, vol. 347, No. 6221, pp. 543-548, Jan. 2015.
Reinhart-King, C., et al., "The Dynamics and Mechanics of Endothelial Cell Spreading," Biophysical Journal, vol. 89, pp. 676-689, Jul. 2005.
Van Vliet, et al., The Biomechanics Toolbox: Experimental Approaches for Living Cells and Biomolecules, Acta Materialia 51: pp. 5881-5905, Aug. 23, 2003, [online], retrieved from the Internet, Oct. 23, 2015.
Batish, M., et al., "Neuronal mRNAs Travel Singly into Dendrites," PNAS, vol. 109(12): pp. 4645-4650 (2012).
Beliveau, B., et al. "Versatile design and synthesis platform for visualizing genomes with Oligopaint FISH probes," PNAS, vol. 109(52): pfa. 21301-21306 (2012).
Bruchez, M., et al., "Semiconductor nanocrystals as fluorescent biological labels," Science, vol. 281, pp. 2013-2016 (1998).
Buckley, P., et al., "Cytoplasmic Intron Sequence-Retaining Transcripts Can Be Dendritically Targeted via ID Element Retrotransposons," Neuron, vol. 69, pp. 877-884 (2011).
Buxbaum, A., et al., Single-Actin mRNA Detection in Neurons Reveals a Mechanism for Regulating Its Translatability, Science, vol. 343, pp. 419-422 (2014).
Cabili, M., et al., "Localization and abundance analysis of human lncRNAs at single-cell and single-molecule resolution," Genome Biology, vol. 16(20) (2015).
Cajigas, I. et al. "The local transcriptome in the synaptic neuropil revealed by deep sequencing and high-resolution imaging," Neuron 74, pp. 453-466 (2012).
Chen, K., et al., "Spatially resolved, highly multiplexed RNA profiling in single cells," Science. vol. 348(6233), aaa6090-aaa6090 (2015).

Choi, H., et al., "Next-Generation in Situ Hybridization Chain Reaction: Higher Gain, Lower Cost, Greater Durability," ACS Nano 8(5): pp. 4284-4294 (2014).
Choi, H. et al., "Programmable in situ amplification for multiplexed imaging of mRNA expression," Nature Biotechnology, 28(11): pp. 1208-1212 (2010).
Chozinski, T., et al., "Expansion microscopy with conventional antibodies and fluorescent proteins,". Nature Methods, vol. 13(6): pp. 485-491 (2016).
Clemson, C., et al., "An architectural role for a nuclear noncoding RNA: NEAT1 RNA is essential for the structure of paraspeckles," Molecular Cell, 33, 717-26 (2009).
Engreitz, J., et al. "The Xist lncRNA exploits three-dimensional genome architecture to spread across the X chromosome," Science 341, 1237973 (2013).
Femino, A., et al., "Visualization of Single RNA Transcripts in Situ," Science, vol. 280; pp. 585-590 (1998).
Feng, G., et al., "Imaging neuronal subsets in transgenic mice expressing multiple spectral variants of GFP," Neuron 28, pp. 41-51 (2000).
Fouz, M., et al., "Bright Fluorescent Nanotags from Bottlebrush Polymers with DNA-Tipped Bristles," ACS Central Science, vol. 1, pp. 431-438 (2015).
Freifeld, et al., Expansion Microscopy of Zebrafish for Neuroscience and Developmental Biology Studies, PNAS, pp. E10799-E10808 (2017).
Huisken, J., et al., "Optical Sectioning Deep Inside Live Embryos by Selective Plane Illumination Microscopy," Science. vol. 305, 1007-1009 (2004).
Jung, H., et al., "Axonal mRNA localization and local protein synthesis in nervous system assembly, maintenance and repair," Nat. Rev. Neurosci., vol. 13(5): pp. 308-324 (2012).
Ke, R., et al., "In situ sequencing for Rna analysis in preserved tissue and cells," Nature Methods, vol. 10(9): pp. 857-860 (2013).
Lee, J., et al., "Highly Multiplexed Subcellular RNA Sequencing in Situ," Science, vol. 343, pp. 1360-1363 (2014).
Lein, E., et al. "Genome-wide atlas of gene expression in the adult mouse brain," Nature, vol. 445, 168-76 (2007).
Levsky, J., et al., "Fluorescence in situ hybridization: past, present and future," Journal of Cell Science, 116, 2833-2838 (2003).
Lieberman-Aiden, E., et al., "Comprehensive mapping of long-range interactions reveals folding principles of the human genome," Science 326, pp. 289-293 (2009).
Lubeck, E., et al., "Single-cell in situ RNA profiling by sequential hybridization," Nature Methods, vol. 11(4): pp. 360-361 (2014).
Lubeck, E., et al., "Single-cell systems biology by super-resolution imaging and combinatorial labeling," Nature Methods, vol. 9, 743-8 (2012).
Mito, M., et al., "Simultaneous multicolor detection of RNA and proteins using super-resolution microscopy," Methods (2015). doi:10.1016/j.ymeth.2015.11.007.
Panning, B., et al., "X chromosome Inactivation is Mediated by by Xist RNA stabilization," Cell. vol. 90, 907-16 (1997).
Plath, K., et al., "Xist RNA and the mechanism of X chromosome inactivation," Annu. Rev. Genet. 36, 233-78 (2002).
Raj, A., et al., "Detection of individual endogenous RNA transcripts in situ using multiple singly labeled probes," Methods in Enzymology, vol. 472, pp. 365-386, (Elsevier Inc., 2010).
Raj, A., et al., Imaging individual mRNA molecules using multiple singly labeled probes. Nat. Methods 5(10: pp. 877-879 (2008).
Schindelin J., et al., "Fiji: an open-source platform for biological-image analysis," Nature Methods, vol. 9, pp. 676-682 (2012).
Shah, S., et al., "Single-molecule RNA detection at depth via hybridization chain reaction and tissue hydrogel embedding and clearing," Development in Review, (2016).
Steward, O., et al., "Compartmentalized synthesis and degradation of proteins in neurons," Neuron, vol. 40, pp. 347-359 (2003).
Steward, O., et al.,Synaptic activation causes the mRNA for the leg Arc to localize selectively near activated postsynaptic sites on dendrites. Neuron, vol. 21, pp. 741-751 (1998).
Thevenaz, P., et al., "A pyramid approach to subpixel registration based on intensity," IEEE Trans. Image Process. 7, 27-41 (1998).

(56) References Cited

OTHER PUBLICATIONS

Tillberg, P., et al., "Protein-Retention Expansion Microscopy of Cells and Tissues Labeled Using Standard Fluorescent Proteins and Antibodies," Nature Biotechnology vol. 34(9): pp. 987-995 (2016).
Wang, F., et al., "RNAscope: A novel in situ RNA analysis platform for formalin-fixed, paraffin-embedded tissues," Journal of Molecular Diagnostics, vol. 14(1): pp. 22-29 (2012).
Zhang, D., et al., "Dynamic DNA nanotechnology using strand-displacement reactions," Nature Chemistry, vol. 3, pp. 103-113 (2011).
Strack, R., "Imaging: Bigger is better for super-resolution," Nature Methods, vol. 12(3), pp. 169-169 (2015).
Cao, W., "DNA Ligases and Ligase-Based Technologies," Clinical and Applied Immunology Reviews 2, pp. 33-43 (2001).

\* cited by examiner cDNA Amplicon Capture ExSEQ:

Reverse Transcription Capture ExSEQ:

RNA Capture EXSEQ:

Legend:

These Steps Take Place Inside Hydrogel

AUGMENTING IN SITU NUCLEIC ACID SEQUENCING OF EXPANDED BIOLOGICAL SAMPLES WITH IN VITRO SEQUENCE INFORMATION

RELATED APPLICATIONS

This application claims the benefit of U.S. Provisional Application No. 62/449,202, filed Jan. 23, 2017, and U.S. Provisional Application No. 62/536,628, filed Jul. 25, 2017 and is a continuation-in-part of U.S. patent application Ser. No. 15/098,968, filed Apr. 14, 2016, which claims the benefit of U.S. Provisional Application No. 62/147,204, filed Apr. 14, 2015. The entire teachings of the above applications are incorporated herein by reference.

GOVERNMENT SUPPORT

This invention was made with Government support under grant numbers 2389114 Life Sciences Research Foundation 3843505, discretionary 6933228, Harvard University 6927725, ML Consortia 6930094, RIC 6934416, HMS 6927725, ML Consortia 6934733, NIH 6929218, NIH 6932279, NIH 6926636, NIH 6928057, ML Consortia 6934493, U-Mich 6935966, Cancer Research UK. The government has certain rights in the invention.

BACKGROUND OF THE INVENTION

Ideally one would be able to identify, and localize, biomolecules such as DNA and RNA throughout all the cells throughout a tissue, with nanoscale precision. Such mechanistic maps would reveal how epigenomic configurations and transcriptomic programs are configured to mediate cellular as well as organ-scale emergent functions, and pathologies. They would also provide systematic datasets that could enable generation of unbiased hypotheses that could be tested via causal perturbation, for a wide variety of basic and applied biological questions.

Current tools do not permit this. Optical methods maintain the spatial location of molecules, but the number of biomolecules that can be studied simultaneously is limited. On the other hand, transcriptomic approaches allow the multiplexed measurement of potentially all the RNA and DNA molecules, but spatial information is lost in the process. For example, in brain tissues all the current RNA sequencing methods involve grinding up or dissociating the neurons before sequencing, thereby destroying all spatial information about the cells in relation to the tissue. Moreover, the subcellular location of the sequences inside the individual cells is also lost, including all the information about the RNA contents of the axons, dendrites, and synapses, which is crucial for the understanding of neuronal communication.

International patent application serial number PCT/US15/16788, which is incorporated herein by reference and Chen et al., *Science,* 347, 543 (2015), teach that the resolution of conventional microscopy can be increased by physically expanding specimens, a process termed 'expansion microscopy' also referred to herein as "ExM". The advantages to ExM include tissue clearing, resolution improvement, and higher tolerance to sectioning error due to the specimen expansion in the z-axis. In the ExM method, cultured cells, fixed tissue, or in principle other types of samples of interest, including biological materials, are infused with a composition, or chemical cocktail, that results in it becoming embedded in the sample material, and then the composition can be expanded isotropically, preferably with nanoscale precision, in three dimensions.

ExM physically magnifies tissues while preserving nanoscale isotropy. It would be desirable to leverage ExM to devise new methods for in situ sequencing of nucleic acids throughout all the cells in a tissue.

SUMMARY OF THE INVENTION

The present invention provides methods for analyzing nucleic acids such as, but not limited to, genomic DNA, RNA, or mRNA. In some embodiments, the disclosure provides a method for preparing and amplifying nucleic acids in situ in a fixed biological sample. The method further comprises amplifying the tagged fragments of nucleic acids.

The invention provides in situ nucleic acid sequencing to be conducted in biological specimens that have been physically expanded. The invention leverages the techniques for expansion microscopy (ExM) to provide methods for in situ sequencing of nucleic acids in a process referred to herein as "expansion sequencing" and also referred to herein as "ExSEQ". However, generating long (>50 bases) sequencing reads in situ is currently challenging. Thus, there is a need for techniques to increase the length of individual spatially-localized in situ sequencing reads, align and improve calling of in situ sequencing libraries, and/or validate the in situ sequencing data.

BRIEF DESCRIPTION OF THE DRAWINGS

The patent or application file contains at least one drawing executed in color. Copies of this patent or patent application publication with color drawings will be provided to the Office upon request and payment of the necessary fee.

DETAILED DESCRIPTION OF THE INVENTION

Figure 1:
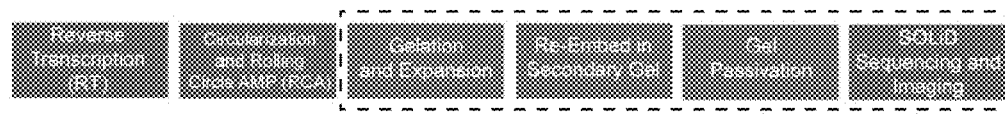
FIG. 1. Schematic illustrating workflows for several expansion sequencing methods in accordance with the invention.
Figure 1:
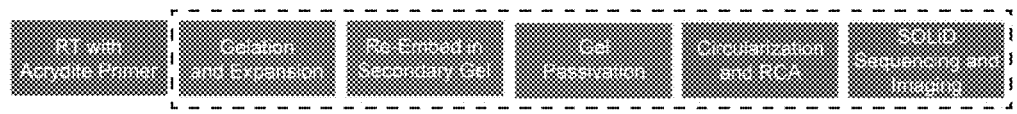
Figure 1:
Figure 1:
Figure 1:

As used herein and in the appended claims, the singular forms "a", "an", and "the" are defined to mean "one or more" and include the plural unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The invention comprises a combination of in situ expansion sequencing (ExSEQ) with in vitro high throughput sequencing technologies (HST) (e.g., Illumina). This in vitro information can be used to increase the length of individual spatially-localized in situ sequencing reads. Furthermore, the HTS can be used as a dictionary to align and improve calling of in situ sequencing libraries. Additionally, the more conventional and widely used in vitro sequencing procedure can be used to validate the in situ sequencing data.

In ExM, chemically fixed and permeabilized tissue is infused with swellable material, undergoes polymerization, and the tissue-polymer composite is treated with protease to homogenize its mechanical characteristics. Next, dialysis in water resulted in a isotropically ~4-fold linear expansion, thereby achieving super-resolution with diffraction-limited microscopes, enabling rapid image acquisition and large field of view (Chen et al., *Science,* 347, 543 (2015)). Expansion allows individual nucleic acids, normally densely packed, to be resolved spatially in a high-throughput manner. Furthermore, the expanded environment is 99% water, facilitating enzyme access and creating "quasi-in vitro" environment while retaining spatial information. Using expansion sequencing (ExSEQ), users can perform the enzymatic sequencing of RNA and DNA directly in expanded cells and tissues, with nanoprecise spatial resolution, enabling systematic cell type and cell state classification in health and disease.

This present invention provides for the development of in situ epigenomic tools. A spatially resolved epigenome would provide details of epigenomic changes mediated by intracellular chromosome conformation. In addition, in situ approaches naturally enable combinatorial measurements from the same sample, including direct interrogation into trans effectors and localization with protein complexes or with measures of gene expression. Notably, these methods may also be applied to spatially resolved 'multi-omic' interrogation of complex tissues to provide a spatially resolved '-omic' understanding of the epigenome.

In one embodiment, the invention provides a method for augmenting the in-situ sequencing of target nucleic acids present in a biological sample with in vitro sequencing of nucleic acids present in a biological sample comprising (i) sequencing, in situ, nucleic acids within a biological sample; (ii) sequencing, in vitro, nucleic acids from a biological sample; and (iii) comparing the in situ sequencing with the in vitro sequencing thereby augmenting the in situ sequencing.

In one embodiment, the invention provides a method for augmenting the in-situ sequencing of target nucleic acids present in a biological sample with in vitro sequencing of nucleic acids present in a biological sample comprising the steps of:

a) attaching target nucleic acids present in the biological sample with a small molecule linker or nucleic acid adapter;

b) embedding the biological sample in a swellable material wherein the small molecule linker or nucleic acid adaptor is attached both to the target nucleic acids present in the sample and to the swellable material;
c) digesting proteins present in the biological sample;
d) swelling the swellable material to form a first enlarged biological sample that is enlarged as compared to the biological sample;
e) optionally re-embedding the first enlarged sample in a non-swellable material;
f) modifying the target nucleic acids or the nucleic acid adaptor to form a target nucleic acids or a nucleic acid adaptor useful for amplifying the nucleic acids and/or sequencing;
g) optionally amplifying the nucleic acids;
h) sequencing, in situ, the nucleic acids;
i) isolating nucleic acid from a biological sample;
j) modifying the target nucleic acids or the nucleic acid adaptor to form a target nucleic acids or a nucleic acid adaptor useful for amplifying the nucleic acids and/or sequencing;
k) sequencing, in vitro, the nucleic acids; and
l) comparing the in situ sequencing with the in vitro sequencing.

In one embodiment, "modifying the target nucleic acids or the nucleic acid adapter" refers to biochemical modification, for example, contacting the target nucleic acids or the nucleic acid adapter with reverse transcriptase.

In one embodiment, the method further comprises repeating steps (a) through (e) on the first enlarged sample to form a second enlarged sample prior to sequencing, a process also known as iterative expansion microscopy (iExM) disclosed in U.S. application Ser. No. 15/098,799 filed on Apr. 14, 2016, and incorporated herein by reference.

In one embodiment, the nucleic acid adaptors are attached to target nucleic acids via ligation to the target nucleic acid. In one embodiment, the nucleic acid adaptors are attached to target nucleic acids via a chemical reagent capable of reacting with amine groups on the target nucleic acid. In one embodiment, the small molecule linkers are attached to target nucleic acids via a chemical reactive group capable of covalently binding the target nucleic acid. In one embodiment, the method further comprises the step of passivating the first swellable material.

The term "nucleic acid" and "polynucleotide" are used interchangeably herein to refer to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. "Nucleic acid" does not refer to any particular length of polymer e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides Additionally, a polynucleotide can be native to the sample (for example, present in the sample at the time the sample is obtained from the original organism). Alternatively, a polynucleotide can be artificial or synthetic, such as when the polynucleotide is added to the sample to cause hybridization to a target nucleic acid. The term "polynucleotide" is intended to include polynucleotides comprising naturally occurring nucleotides and/or non-naturally occurring nucleotides. Non-naturally occurring nucleotides can include chemical modifications of natural nucleotides. In this case, it is preferred that the synthetic polynucleotides can hybridize to the tagged genomic fragments.

The term "sequence," in reference to a nucleic acid, refers to a contiguous series of nucleotides that are joined by covalent bonds (e.g., phosphodiester bonds).

The term "target nucleic acid" refers to a nucleic acid whose presence in a sample may be identified and sequenced. A target nucleic acid can be any nucleic to be selected and, optionally, amplified or sequenced preferably in combination with the nucleic acid adaptor. Target nucleic acids for use in the provided methods may be obtained from any biological sample using known, routine methods.

As used herein, the term "biological sample" means any biological sample that comprises, or is believed to comprise, nucleic acid sequences including, but not limited to cDNA, mRNA and genomic DNA. Exemplary biological samples include, but are not limited to tissues, including but not limited to, liver, spleen, kidney, lung, intestine, thymus, colon, tonsil, testis, skin, brain, heart, muscle and pancreas tissue. Other exemplary biological samples include, but are not limited to, biopsies, bone marrow samples, organ samples, skin fragments and organisms. Materials obtained from clinical or forensic settings are also within the intended meaning of the term biological sample. In one embodiment, the sample is derived from a human, animal or plant. In one embodiment, the biological sample is a tissue sample, preferably an organ tissue sample. In one embodiment, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g., bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased), or considered normal or healthy.

The term "fixed biological sample" is used herein in a broad sense and is intended to include sources that contain nucleic acids and can be fixed. As used herein, the term "fixed biological sample", explicitly excludes cell-free samples, for example cell extracts, wherein cytoplasmic and/or nuclear components from cells are isolated.

Fixation of the biological sample can be effected with fixatives known to the person skilled in the art. In one embodiment, the fixative, includes but is not limited to, acids, alcohols, ketones or other organic substances, such as, glutaraldehyde, formaldehyde or paraformaldehyde. Examples of fixatives and uses thereof may be found in Sambrook et al. (2000) and Maniatis et al. (1989). In one embodiment, the used fixation also preserves DNA and RNA. According to one embodiment of the process according to the invention, a formaldehyde-fixed, paraffin-embedded biological sample (FFPE sample) is used. Other fixatives and fixation methods for providing a fixed biological sample are known in the prior art. For example, the biological sample can be fresh froze, wherein alcohol based fixed samples can be used. In one embodiment, the fixed tissue may or may not be embedded in a non-reactive substance such as paraffin. In one embodiment, the fixed tissue may or may not be embedded in an unswellable hydrogel. Embedding materials include, but are not limited to, paraffin, mineral oil, non-water soluble waxes, celloidin, polyethylene glycols, polyvinyl alcohol, agar, gelatine, nitrocelluloses, methacrylate resins, epoxy resins or other plastic media. Thereby, one can produce tissue sections of the biological material suitable for histological examinations.

Alternatively or additionally, the fixed biological sample can be an expandable biological sample. In one embodiment, fixation of the biological sample can be effected by embedding the sample in a swellable material that has been perfused throughout the sample as described by Chen et al. (Chen et al., *Science*, 347, 543 (2015) and U.S. Patent Publication Nos. US 2016-0116384-A1; US 2016-0305856-A1; US 2016-0304952-A1; and U.S. patent application Ser. Nos. 15/229,539 and 15/229,545 incorporated herein by reference in their entirety). Briefly, a sample, such as tissue, can be permeabilized. A permeabilized sample, or tissue, can be infused with monomers or precursors of a swellable material and then causing the monomers or precursors to undergo polymerization within the sample to form the swellable material. During or after polymerization, the swellable material can be anchored or cross-linked (e.g., covalently crosslinked) to the sample. The sample-swellable material complex is optionally treated with protease to homogenize the mechanical characteristics of the sample. The sample-swellable material complex can then be treated by dialysis in a solvent or liquid, such as in water, resulting in isotropic physical expansion of the sample. In this manner, the fixed biological sample is physically "enlarged", or "expanded", as compared to the biological sample before swelling.

In one embodiment, the swellable material is a hydrogel. In one embodiment, the hydrogel is a polyelectrolyte hydrogel. In one embodiment, the polyelectrolyte is a polyacrylate.

In some embodiments, the sample is embedded in a swellable or unswellable hydrogel following permeabilization of the fixed biological sample. Embedding the sample at this stage limits the diffusion of unfixed fragments.

In some embodiments, the sample is embedded in a swellable or unswellable hydrogel following transposition. Embedding the sample at this stage limits the diffusion of the tagged fragments of genomic DNA. Additionally, embedding the sample at this stage allows for embedding the tagged fragments of genomic DNA in the hydrogel as well if the adaptors molecules comprise a polymerizable group.

In some embodiments, the sample is embedded in a swellable or unswellable hydrogel following circularization. Embedding the sample at this stage allows for embedding the tagged fragments of genomic DNA in the hydrogel as well if the hairpin has a polymerizable group.

In some embodiments, the sample is embedded in a swellable or unswellable hydrogel following amplification. Embedding the sample at this stage allows for embedding of the amplicons in the hydrogel as well to permit digestion and sample clearing from the fixed biological sample.

In some embodiments, the enlarged sample can be re-embedded in a non-swellable material. "Re-embedding" comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the first enlarged sample, for example, is embedded in the non-swellable material. Embedding the expanded sample in a non-swellable material prevents conformational changes during sequencing despite salt concentration variation. The non-swellable material can be charge-neutral hydrogels. For example, it can be polyacrylamide hydrogel, composed of acrylamide monomers, bisacrylamide cross-linker, ammonium persulfate (APS) initiator and tetramethylethylenediamine (TEMED) accelerator.

The expandable biological sample can be expanded prior to or after the treating step, amplification step or after the optional ligation step. In other words, the step of expanding the biological sample can be independently performed before or after the treating step, amplification step or ligation step. In view of the flexibility in the order of the performing each step, the article "a" is used to describe the biological sample in each step to ensure that, in each instance, the biological sample is not necessarily the product produced by the preceding step.

As used herein, the term "attach" or "attached" refers to both covalent interactions and noncovalent interactions. In certain embodiments of the invention, covalent attachment may be used, but generally all that is required is that the nucleic acids remain attached to the target nucleic acid under conditions for nucleic acid amplification and/or sequencing. Typically, oligonucleotide adaptors are attached such that a 3' end is available for enzymatic extension and at least a portion of the sequence is capable of hybridizing to a complementary sequence. Attachment can occur via hybridization to the target nucleic acid, in which case the attached oligonucleotide may be in the 3'-5' orientation. Alternatively, attachment can occur by means other than base-pairing hybridization, such as the covalent attachment set forth above. The term "attach" may be used interchangeably herein with the terms, "anchor(ed)", affix(ed), link(ed) and immobilize(d).

As used herein, a "nucleic acid adaptor" is a nucleic acid sequence capable of attaching to a target nucleic acid and to the swellable material of the expansion gel. In one embodiment, attaching nucleic acid molecules to a target nucleic acid may be accomplished by ligation in situ. For example, anchorable DNA adaptors may be ligated to the 3' ends of the RNAs in the sample with RNA ligases, such as T4 RNA ligase, or may be attached via a chemical linker such as a reactive amine group capable of reacting with target nucleic acid. Additionally, acrylamide modified oligonucleotide primers may be covalently fixed within a swellable material such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule capable of attaching to a target nucleic acid and to the swellable material of the expansion gel. In one embodiment, attaching the small molecule to the target nucleic acid may be accomplished by chemical reactive group capable of covalently binding the target nucleic acid. For example, LABEL-IT® Amine (MirusBio) is a small molecule with alkylating group that primarily reacts to the N7 of guanine, thereby allowing covalent binding of RNA and DNA. Additionally, the small molecule (for example, LABEL-IT®) can be acrylamide modified and therefore may be covalently fixed within a swellable material such as a polyacrylate gel. As used herein, the term "acrylamide modified" in reference to a small molecule linker means that the small molecule has an acrylamide moiety.

The term "biochemically modifying the target nucleic acids or the nucleic acid adaptor to form a target nucleic acids or a nucleic acid adaptor useful for sequencing" as used herein refers to converting the target nucleic acids or the nucleic acid adaptor to cDNA via reverse transcriptase, if necessary, and then circularizing the cDNA followed by subsequent amplification.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

Sequencing can be carried out by any method known in the art including, but not limited to, sequencing by hybridization, sequencing by ligation or sequencing by synthesis. General sequencing methods known in the art, such as sequencing by extension with reversible terminators, fluorescent in situ sequencing (FISSEQ), pyrosequencing, massively parallel signature sequencing (MPSS) and the like are suitable for use in the methods of the invention. Reversible termination methods use step-wise sequencing-by-synthesis biochemistry that coupled with reversible termination and removable fluorescence.

FISSEQ is a method whereby DNA is extended by adding a single type of fluorescently-labelled nucleotide triphosphate to the reaction; washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described, for example in, (Lee et al., *Science*. 343, 1360-3 (2014)).

Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) *Science* 281:363.

MPSS utilizes ligation-based DNA sequencing simultaneously. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al., (2000) *Nat. Biotech.* 18:630.

In one embodiment, the biological sample can be labeled or tagged preferably with a detectable label. Typically, the label or tag will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis. Thus, the detectable label is preferably chemically attached to the biological sample, or a targeted component thereof. In one embodiment, the detectable label is an antibody and/or fluorescent dye wherein the antibody and/or fluorescent dye, further comprises a physical, biological, or chemical anchor or moiety that attaches or crosslinks the sample to the composition, hydrogel or other swellable material. In one embodiment, the detectable label is attached to the nucleic acid adaptor. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

As used herein, the term "swellable material" generally refers to a material that expands when contacted with a liquid, such as water or other solvent. In one embodiment, the swellable material uniformly expands in 3 dimensions. Additionally or alternatively, the material is transparent such that, upon expansion, light can pass through the sample. In one embodiment, the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N, N-alkylene bisacrylamides). Precursors can also comprise polymerization initiators and crosslinkers.

In a preferred embodiment, the swellable polymer is polyacrylate or polyacrylamide and copolymers or crosslinked copolymers thereof. Alternatively or additionally, the swellable material can be formed in situ by chemically crosslinking water soluble oligomers or polymers. Thus, the invention envisions adding precursors (such as water soluble precursors) of the swellable material to the sample and rendering the precursors swellable in situ.

In one embodiment, "embedding" the sample in a swellable material comprises permeating (such as, perfusing, infusing, soaking, adding or other intermixing) the sample with the swellable material, preferably by adding precursors thereof. Alternatively or additionally, embedding the sample in a swellable material comprises permeating one or more monomers or other precursors throughout the sample and polymerizing and/or crosslinking the monomers or precursors to form the swellable material or polymer. In this manner the biological sample is embedded in the swellable material.

In one embodiment, a biological sample, or a labeled sample, is permeated with a composition comprising water soluble precursors of a water swellable material and reacting the precursors to form the water swellable material in situ.

In one embodiment, the "re-embedding" comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the first enlarged sample, for example, is embedded in the non-swellable material. Embedding the expanded sample in a non-swellable material prevents conformational changes during sequencing despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

In one embodiment, the biological sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

As used herein the term "gel passivation" refers to the process for rendering a gel less reactive with the components contained within the gel such as by functionalizing the gel with chemical reagents to neutralize charges within the gel. For example, the carboxylic groups of sodium acrylate, which may be used in the swellable gel, can inhibit downstream enzymatic reactions. Treating the swellable gel composed of sodium acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel. After re-embedding in the non-swellable gel, the swellable gel may also be partially or completely degraded chemically, provided that the target nucleic acids can either stay anchored or can be transferred to the non-swellable gel.

In one embodiment, the biological sample and each enlarged sample thereafter is permeated with one or more monomers or a solution comprising one or more monomers or precursors which are then reacted to form a swellable or non-swellable polymerized gel depending on what step of the method is being performed. For example, if the biological sample is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

Once the sample, or labeled sample, is permeated, the solution is activated to form sodium polyacrylate. In one embodiment, the solution comprising the monomers is aqueous. The solution is preferably at high concentration, such as about 50% or more saturation (defined herein as the percentage of solids present in the aqueous solvent in the same ratio as would result in precipitation under the conditions of permeation). The solution is preferably at high concentration, such as about 75% or more saturation, more preferably 90% or more saturation.

In one embodiment, after the biological sample has been anchored to the swellable material, the sample is, optionally, subjected to a disruption of the endogenous biological molecules (or the physical structure of the biological sample, where the sample is other than a biological material), leaving the target nucleic acids with a small molecule linker or nucleic acid adapter, and the detectable labels such as fluorescent dye molecules, intact and anchored to the swellable material. In this way, the mechanical properties of the sample-swellable material complex are rendered more spatially uniform, allowing isotropic expansion with minimal artifacts.

As used herein, the "disruption of the endogenous physical structure of the sample" or the term "disruption of the endogenous biological molecules" of the biological sample generally refers to the mechanical, physical, chemical, biochemical or, enzymatic digestion, disruption or break up of the sample so that it will not resist expansion. In one embodiment, a protease enzyme is used to homogenize the sample-swellable material complex. It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample. In one embodiment, the disruption of the physical structure of the sample is protein digestion of the proteins contained in the biological sample.

The sample-swellable material complex is then isoptropically expanded. In one embodiment, a solvent or liquid is added to the complex which is then absorbed by the swellable material and causes swelling. Where the swellable material is water swellable, an aqueous solution can be used.

In one embodiment, the addition of water allows for the embedded sample to expand at least 3 times, preferably 4 times, preferably 5 times, or more its original size in three-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. Surprisingly, as the material swells isotropically, the anchored tags maintain their relative spatial relationship.

The swollen material with the embedded biological sample can be imaged on any optical microscope, allowing effective imaging of features below the classical diffraction limit. Since the resultant specimen is transparent, custom microscopes capable of large volume, Widefield of view, 3D scanning may also be used in conjunction with the expanded sample. The method also provides an optional step comprising amplification of the detectable label.

In accordance with the invention, chemically fixed and permeabilized biological specimens are embedded in a swellable gel material, subjected to a treatment to disrupt native biological networks, and then expanded. A sequence of enzymatic and/or chemical steps are carried out in order to anchor the target molecules into the swellable material and to prepare them for the sequencing reactions. Expansion can be carried out at one of several points in the sequence of preliminary reactions. The expanded gel is finally converted while expanded to a non-expanding state, by re-embedding in a non-expanding material. RNA or DNA molecules present in the sample may be sequenced using methods known to those familiar with the art, including sequencing by hybridization, ligation, and synthesis.

Nucleic Acid Anchoring:

For the FISSEQ process to be compatible with ExM, first nucleic acids, especially RNAs, cDNA, and/or DNA, have to be incorporated into the hydrogel network. We established two strategies for accomplishing this:

Ligation: DNA or RNA adapters with hydrogel anchorable groups (e.g. acrydite, 6-((Acryloyl)amino) hexanoic acid (Acryloyl-X) (Life Technologies)) can be ligated in situ. For example, anchorable DNA adaptors may be ligated to the 3' ends of the RNAs in the sample with RNA ligases, such as T4 RNA ligase. This can be done after RNA fragmentation (e.g., using RNase III), so that the resulting RNA fragments are short (~200-500 bases long) and contain 3'OH, which allows ligation with minimal side effects. In certain incarnations, these anchoring adapters may have additional roles in the preparation of the sequencing substrate, such as priming PCR or reverse transcription.

Anchoring in Via Chemical Reagents:

The commercial chemical reagent Label-IT® Amine (Mirus Bio LLC), modified with hydrogel anchorable groups, (e.g., 6-((Acryloyl)amino)hexanoic acid (Acryloyl-X) (Life Technologies)), can be used for covalently securing RNA and DNA molecules directly to the ExM gel. The chemical and ligation approaches can also be used together. For example, the RNA or DNA can be anchored to the expanded gel with LABEL-IT® and then, in the expanded state, the RNA or DNA can be fragmented and ligated with RNA or DNA adapters.

In addition to the initial anchoring, the targets or any downstream products may be anchored at any point including in the native state or following any number of biochemical modifications such as reverse transcription or rolling circle amplification used to prepare targets for in situ sequencing (see FIG. 1).

Hydrogel Embedding:

Hydrogel embedding and expansion of tissue can be performed as described in ExM (International patent application serial number PCT/US15/16788 and Chen et al., Science, 347, 543 (2015)). Briefly: Monomer solution including sodium acrylate, acrylamide, and bisacrylamide, salt and buffer is mixed and prior to embedding, monomer solution is cooled to 4° C. to prevent premature gelation. Ammonium persulfate (APS) initiator and tetramethylethylenediamine (TEMED) accelerator are added to the monomer solution up to 0.2% (w/w) each. For thick specimens, the inhibitor 4-hydroxy-2,2,6,6-tetramethylpiperidin-1-oxyl (4-hydroxy-TEMPO) can be added to inhibit gelation during diffusion of the monomer solution into tissue sections. Cells or tissue slices can be incubated with the monomer solution plus APS/TEMED (and 4-hydroxy-TEMPO for thick sections) at 4° C. (for variable time depending on thickness) to allow monomer solution to diffuse, and then transferred to a humidified 37° C. incubator for 1-2 hours.

Alternative gel recipes, varying in monomer, crosslinker, initiator, accelerator, inhibitor and other additives can be used to tune the hydrogel properties such as expansion factor, chemical environment, and mechanical properties. These monomers include, acrylamide variants such as dimethylacrylamide, hydroxymethylacrylamide and acrylamide. Other free radical initiators such as VA-044 or UV activated (irgacure, riboflavin) may also be used.

Tissue Digestion, Expansion and Re-Embedding:

The cells are homogenized via proteolysis before the expansion. Proteinase K in digestion buffer (50 mM Tris (pH 8), 1 mM EDTA, 0.5% Triton X-100, 0.8 M guanidine HCl) can be applied directly to gels in at least ten times volume excess. The gels are then incubated in digestion buffer for at least 12 hours. During this step, formaldehyde crosslinks may also be reversed through heat, pH or chemical treatments.

Alternative methods of tissue disruption can be used, such as base or acid hydrolysis, and alternative proteinases. Digested gels can be next placed in excess volumes of doubly de-ionized water to expand. The expanded hydrogel, in the expanded state, is re-embedded within a non-expanding gel to prevent gel conformational changes during sequencing. For example, the non-expanding gel can be composed of acrylamide monomers, bisacrylamide, ammonium persulfate (APS) initiator and tetramethylethylenediamine (TEMED) accelerator.

Expanding Gel Passivation:

The carboxylic groups of sodium acrylate, used in the expanding gel, can inhibit downstream enzymatic reactions. Treating the sample with 1-Ethyl-3-(3-dimethylaminopropyl)carbodiimide (EDC) and N-Hydroxysuccinimide (NHS) allows primary amines, as ethanolamine, to covalently bind the carboxylic groups and passivate the expanding gel. The expanding gel may also be degraded chemically, after re-embedding in the non-expanding gel, provided that the anchored moieties are transferred to the re-embedding gel. Use of alternative non-charged hydrogel chemistries may also avoid charge passivation.

Incorporating FISSEQ Steps:

Following expansion, re-embedding and passivation, FISSEQ enzymatics steps can be carried out as previously described (Lee et al., Science. 343, 1360-3 (2014)). FISSEQ steps can be integrated for expansion at a variety of steps, see FIG. 1 for how the FISSEQ step order can be incorporated with expansion steps. Briefly, the anchored RNA is further biochemically modified into an in situ sequence-able substrate via reverse transcription, circularization of the cDNA, and subsequent amplification by phi29 polymerase, methods known to those familiar with the art. Sequencing by ligation or synthesis is used to identify the endogenous cDNA amplicons, and the molecules are also localized in 3D space. Localization may be converted into pre-expansion space using simple scaling transformations.

In some embodiments, the invention provides methods for analyzing polynucleotides such as genomic DNA. In some embodiments, the disclosure provides a method for preparing and amplifying a genomic DNA library in situ in a fixed biological sample. The method comprises treating a fixed biological sample with an insertional enzyme complex to produce tagged fragments of genomic DNA. As used herein, in situ generally refers to wherein the tagged fragments are present at their original place (in-situ), i.e., within the cell or tissue, thereby aiding in localizing the sequence within the sample. In some embodiments, the method further comprises circularizing the tagged fragments of genomic DNA. In some embodiments, the method further comprises amplifying the tagged fragments of genomic DNA.

In some embodiments, the genomic library is constructed from accessible chromatin. In some embodiments, the genomic library is constructed from the whole genome.

The term "insertional enzyme complex," as used herein, refers to a complex comprising an insertional enzyme and at least two adaptor molecules (the "transposon tags") that are combined with polynucleotides to fragment and add adaptors to the polynucleotides. In some embodiments, the accessible chromatin or whole genome may be fragmented into a plurality of fragments during the insertion of the molecular tags. In this step, the chromatin or whole genome is tagmented (i.e., cleaved and tagged in the same reaction) using an insertional enzyme such as a transposase that cleaves the genomic DNA in open regions in the chromatin and adds adaptors to both ends of the fragments. Methods for tagmenting isolated genomic DNA are known in the art (see, e.g., Caruccio Methods Mol. Biol. 2011 733: 241-55; Kaper et al, Proc. Natl. Acad. Sci. 2013 110: 5552-7; Marine et al, Appl. Environ. Microbiol. 2011 77: 8071-9, US20100120098 and US20160060691) and are commercially available from Illumina (San Diego, Calif.) and other vendors. Such systems may be readily adapted for use herein. In some cases, the conditions may be adjusted to obtain a desirable level of insertion in the chromatin or whole genome (e.g., an insertion that occurs, on average, every 50 to 200 base pairs in open regions).

The insertional enzyme can be any enzyme capable of inserting a nucleic acid sequence into a polynucleotide. In some cases, the insertional enzyme can insert the nucleic acid sequence into the polynucleotide in a substantially sequence-independent manner. The insertional enzyme can be prokaryotic or eukaryotic. Examples of insertional enzymes include, but are not limited to, transposases, HERMES, and HIV integrase. The transposase can be a Tn transposase (e.g., Tn3, Tn5, Tn7, Tn10, Tn552, Tn903), a MuA transposase, a Vibhar transposase (e.g., from Vibrio

*harveyi*), Ac-Ds, Ascot-1, Bsl, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, TnlO, Tyl, any prokaryotic transposase, or any transposase related to and/or derived from those listed above. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, Ca2+, Mg2+ and Mn2+.

The adaptor molecules can comprise additional sequences that can be used for amplification, detection and/or sequencing. Such additional sequences can include, but are not limited to, sequencing adaptors, primer binding sites, locked nucleic acids (LNAs), zip nucleic acids (ZNAs), RNAs, affinity reactive molecules (e.g., biotin, dig), self-complementary molecules, phosphorothioate modifications, DNA tags, barcodes, and azide or alkyne groups. In some embodiments, the sequencing adaptors can further comprise a barcode label. Further, the barcode labels can comprise a unique sequence. The unique sequences can be used to identify the individual insertion events. Any of the tags can further comprise fluorescence tags (e.g., fluorescein, rhodamine, Cy3, Cy5, thiazole orange, etc.).

In some embodiments, the adaptor molecules can comprise unmodified DNA oligonucleotides. Examples of such unmodified DNA oligonucleotides include, but are not limited to, oligonucleotides consisting of the 19 basepair mosaic end Tn5 transposase recognition sequence, oligonucleotides which contain the recognition sequence as a subsequence as well as containing an additional sequence as a subsequence (e.g., Illumina Read 1 or Read 2 or any user-defined sequence). In some embodiments, the adaptor molecules can comprise modified DNA oligonucleotides. As used herein, "modified DNA oligonucleotides" refer to oligonucleotides which contain a chemical modification on the 5' end, the 3' end, or internally, and/or oligonucleotides that incorporate non-standard DNA bases (e.g., uracil, xenonucleic acids). Examples of such modified DNA oligonucleotides include, but are not limited to, 5' or 3' phosphorylation, 5' acrydite modification, internal methacrylate functionalized uracil.

In some embodiments, the insertional enzyme can comprise two or more enzymatic moieties wherein each of the enzymatic moieties inserts a common sequence into the accessible chromatin or whole genome. The enzymatic moieties can be linked together. The common sequence can comprise a common barcode. The enzymatic moieties can comprise transposases. The accessible chromatin or whole genome can be fragmented into a plurality of fragments during step (a), wherein the fragments comprising the common barcode are determined to be in proximity in the three-dimensional structure of the polynucleotide.

In some embodiments, the tagged fragments of genomic DNA can be circularized. Circularization of the tagged fragments of genomic DNA can be accomplished by any suitable method known to one skilled in the art including, but not limited to, oligonucleotide displacement, hairpin hybridization, gap repair, and ligation. For example, the biological sample is exposed to a ligase and upon recognition of and hybridization to the tagged fragments of genomic DNA the 5' end and the 3' end of tagged fragments of genomic DNA are ligated to each other through the action of the ligase, forming a circular structure. In other words, the 5' end and the 3' end of a tagged fragment are brought into juxtaposition, forming a circle, which allows the ends to be covalently joined by the action of a ligase. As the tagged fragments comprise genomic DNA, the ligation products are in the form of a circle of double-stranded genomic DNA.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between 5' carbon of a terminal nucleotide of the tagged fragment of genomic DNA with the 3' carbon of the tagged fragment of genomic DNA.

A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) Nucl. Acids Res. 27:875; Higgins et al., Meth. in Enzymol. (1979) 68:50; Engler et al. (1982) The Enzymes, 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids Research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include SplintR ligase, T4 DNA ligase, T7 DNA ligase, *E. coli* DNA ligase, Taq ligase, Pfu ligase and the like. Certain protocols for using ligases are disclosed by the manufacturer and also in Sambrook, Molecular Cloning: A Laboratory manual, 2.sup.nd Edition (Cold Spring Harbor Laboratory, New York, 1989); Barany, PCR Methods and Applications, 1:5-16 (1991); Marsh et al., Strategies, 5:73-76 (1992). In one embodiment, the ligase may be derived from algal viruses such as the Chlorella virus, for example, PBCV-1 ligase, also known as SplintR ligase, as described U.S. Patent Publication No. 2014/0179539, incorporated herein by reference in its entirety.

In some embodiments, the method further comprises amplifying the tagged fragments of genomic DNA. The expression "amplification" or "amplifying" refers to a process by which extra or multiple copies of a particular polynucleotide are formed. The term "amplification product" refers to the nucleic acids, which are produced from the amplifying process as defined herein.

Amplification includes methods generally known to one skilled in the art such as, but not limited to, PCR, ligation amplification (or ligase chain reaction, LCR), real time (rtPCR) or quantitative PCR (qPCR), rolling circle amplification (RCA), and other amplification methods. These methods are generally known. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In one embodiment, the ligation product is amplified using PCR. In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e., each primer is specifically designed to be complementary to each strand of the genomic locus to be amplified. In one embodiment, the tagged fragments of genomic DNA are amplified using qPCR. Quantitative polymerase chain reaction is used to simultaneously detect a specific DNA sequence in a sample and determine the actual copy number of this sequence relative to a standard. In one embodiment, the tagged fragments of genomic DNA are amplified using rtPCR. In real-time PCR, the DNA copy number can be established after each cycle of amplification. By using a fluorescent reporter in the reaction, it is possible to measure DNA generation.

In one embodiment, the tagged fragments of genomic DNA are amplified using Rolling circle amplification (RCA). RCA describes a process of unidirectional nucleic acid replication that can rapidly synthesize multiple copies of circular molecules of DNA or RNA.

In some embodiments, the tagged fragments can be sequenced to generate a plurality of sequencing reads. This may be used to determine the accessibility of the polynucleotide at any given site. The fragments may be sequenced using a high-throughput sequencing technique. In some cases, the sequencing reads can be normalized based on the sequence insertion preference of the insertional enzyme. The length of the sequenced reads can be used to determine a chromatin state annotation.

Additionally, the insertional enzyme complex can further comprise an affinity tag. In some cases, the affinity tag can be an antibody. The antibody can bind to, for example, a transcription factor, a modified nucleosome or a modified nucleic acid. Examples of modified nucleic acids include, but are not limited to, methylated or hydroxymethylated DNA. In other cases, the affinity tag can be a single-stranded nucleic acid (e.g., ssDNA, ssRNA). In some examples, the single-stranded nucleic acid can bind to a target nucleic acid. In further cases, the insertional enzyme complex can further comprise a nuclear localization signal.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. Assessing the presence of includes determining the amount of something present, as well as determining whether it is present or absent.

Through suitable design of a probe sequence outside the tagged portion of the genomic DNA, detection may be performed through various methods. One example is loop-mediated isothermal amplification (LAMP), wherein probes are designed to form LAMP target structures upon ligation (Notomi, et al., Nucleic Acids Res., 28(12): e63 (2000)). Presence of target nucleic acid is then detected via LAMP amplification, enabling advantages such as isothermal reaction conditions, rapid detection, and implementation in field or point-of-care diagnostics. Upon successful ligation, detection of amplification of target nucleic acid via may be performed with traditional qPCR dyes and probes as described above, or with additional methodologies: turbidity detection of precipitated magnesium pyrophosphate (Mori, et. al., Biochem. Biophys. Res. Commun., 289:150-154 (2001)); colorimetric detection using metal-sensitive indicators (Tomita, et. al., Nat. Protocols, 3(5):877-82 (2008); Goto, et al., BioTechniques, 46(3):167-71 (2009)); bioluminescence through pyrophosphate conversion (Gandelman, et al., PLoS One, 5: e14155 (2010)); or detection via change in pH due to amplification in weakly-buffered conditions (Pourmand, et. al., PNAS, 103(17):6466-70 (2006); U.S. Pat. No. 7,888,015; and U.S. patent application Ser. No. 13/799,995.

After the chromatin has been fragmented and tagged to produce tagged fragments of genomic DNA, at least some of the adaptor tagged fragments are sequenced to produce a plurality of sequence reads. The fragments may be sequenced prior to or after the ligation step. Additionally or alternatively, the fragments may be sequenced prior to or after the amplification step using any convenient method.

The present invention further provides a method for analyzing chromatin in situ in a fixed biological sample. The method comprising (a) preparing a genomic library as described herein; and (b) sequencing all or a portion of the tagged fragments to produce a plurality of sequence reads. The information obtained from the sequence reads can be used for making an epigenetic map of the genome, or a region thereof, of the fixed sample in situ by mapping the information to the genome, or region thereof.

The present disclosure also provides a method for analyzing the three-dimensional structure of a polynucleotide from a fixed biological sample in situ, comprising: preparing a genomic library as described herein; and using the molecular tags to analyze the three-dimensional structure of the polynucleotide. In some embodiments, the insertional enzyme can comprise two or more enzymatic moieties, which may be optionally linked together. The enzymatic moieties can be linked by using any suitable chemical synthesis or bioconjugation methods. For example, the enzymatic moieties can be linked via an ester/amide bond, a thiol addition into a maleimide, Native Chemical Ligation (NCL) techniques, Click Chemistry (i.e., an alkyne-azide pair), or a biotin-streptavidin pair. In some embodiments, each of the enzymatic moieties can insert a common sequence into the polynucleotide. The common sequence can comprise a common barcode. The enzymatic moieties can comprise transposases or derivatives thereof. In some embodiments, the genomic DNA may be fragmented into a plurality of fragments during the insertion. The fragments comprising the common barcode can be determined to be in proximity in the three-dimensional structure of the polynucleotide.

In some embodiments, DNA fragments corresponding to one or more regions of a genome (e.g., 2 or more, 10 or more, 50 or more, 100 or more, up to 1,000 or more regions) may be enriched, i.e., selected, by hybridization prior to sequencing. In these embodiments, the entire library does not need to be sequenced. Depending on the desired result and length of the selected region (if a selection step has been performed), this step of the method may result in at least 1,000 sequencing (e.g., at least 10,000, at least 100,000, at least 500,000, at least 106, at least 5×106, up to 107 or more sequencing reads). The sequence reads are generally stored in computer memory.

Some embodiments of the methods involve making an epigenetic map of a region of the genome of the fixed biological sample in situ. This step may be done by sequencing all or a portion of the tagged fragments of genomic DNA and mapping information obtained from the sequence reads to the region. In these embodiments, the sequence reads are analyzed computationally to produce a number of numerical outputs that are mapped to a representation (e.g., a graphical representation) of a region of interest. Many types of information may be mapped, including, but not limited to: (i) cleavage sites for the transposase; (ii) the sizes of the fragments produced in step a); (iii) fragment length; (iv) the positions of sequence reads of a defined range in length; and (v) sequence read abundance.

The resultant epigenetic map can provide an analysis of the chromatin in a region of interest. For example, depending on which information is mapped, the map can show one or more of the following: a profile of chromatin accessibility along the region; DNA binding protein (e.g., transcription factor) occupancy for a site in the region; nucleosome-free DNA in the region; positioning of nucleosomes along the region; and a profile of chromatin states along the region. In some embodiments, the method may further comprise measuring global occupancy of a binding site for the DNA binding protein by, e.g., aggregating data for one DNA binding protein over a plurality of sites to which that protein binds. In certain instances, the map can also be annotated with sequence information, and information about the sequence (e.g., the positions of promoters, introns, exons, known enhancers, transcriptional start sites, untranslated regions, terminators, etc.) so that the epigenetic information can be viewed in context with the annotation.

In certain embodiments, the epigenetic map can provide information regarding active regulatory regions and/or the transcription factors that are bound to the regulatory regions. For example, nucleosome positions can be inferred from the lengths of sequencing reads generated. Alternatively, transcription factor binding sites can be inferred from the size, distribution and/or position of the sequencing reads generated. In some embodiments, transcription factor binding sites can be inferred from sequencing reads generated. In other embodiments, transcription factors can be inferred from sequencing reads generated.

The method described above may also be used as a diagnostic (which term is intended to include methods that provide a diagnosis as well as methods that provide a prognosis). These methods may comprise, e.g., analyzing chromatin from a patient using the methods described herein to produce an epigenetic map; and providing a diagnosis or prognosis based on the epigenetic map.

The method set forth herein may be used to provide a reliable diagnostic to any condition associated with altered chromatin or DNA binding protein occupancy. The method can be applied to the characterization, classification, differentiation, grading, staging, diagnosis, or prognosis of a condition characterized by an epigenetic pattern (e.g., a pattern of chromatin accessibility or DNA binding protein occupancy). For example, the method can be used to determine whether the epigenetic map of a sample from an individual suspected of being affected by a disease or condition is the same or different compared to a sample that is considered "normal" with respect to the disease or condition. In particular embodiments, the method can be directed to diagnosing an individual with a condition that is characterized by an epigenetic pattern at a particular locus in a test sample, where the pattern is correlated with the condition. The methods can also be used for predicting the susceptibility of an individual to a condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

In some embodiments, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

In yet another aspect, the present disclosure provides kits that contain reagents for practicing the subject methods, as described herein. The subject kits can comprise a transposase and transposon tags, and a transposase reaction buffer, wherein the components of the kit are configured such that, combining the reaction buffer, transposase and adaptors with a fixed biological sample results in the production of adaptor-tagged fragments of genomic DNA.

In some cases, the kit can comprise an insertional enzyme comprising an affinity tag; and an insert element comprising a nucleic acid, wherein said nucleic acid comprises a predetermined sequence. The insertional enzyme can be, for example, a transposase. The insertional enzyme can also comprise two or more enzymatic moieties that are linked together. In some cases, the affinity tag can be an antibody. The antibody can bind to a transcription factor, a modified nucleosome, or a modified nucleic acid. Examples of modified nucleic acids include, but are not limited to, methylated or hydroxymethylated DNA. In other cases, the affinity tag can be a single-stranded nucleic acid (e.g., ssDNA, ssRNA).

The kit may optionally contain other components, for example: PCR primers, PCR reagents such as polymerase, buffer, nucleotides etc., as described above. The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences.

The term "barcode sequence" or "molecular barcode," as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "chromatin," as used herein, refers to a complex of molecules including proteins and polynucleotides (e.g., DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

The term "treating," as used herein, refers to combining under conditions (e.g., a suitable temperature, time and conditions) that result in a reaction, (e.g., cleavage).

The term "transcription factor", as used herein, refers to any polypeptide that may act by itself or in combination with at least one other polypeptide to regulate gene expression levels. The term includes, but is not limited to, polypeptides that directly bind DNA sequences. Transcription factors can either increases or suppress expression levels. Examples of transcription factors include, but are not limited to Myc/Max, AP-1 (Jun, Fos, ATF), CREB, SMAD, HIF, ETS, ERG, ELK, STAT, estrogen receptor (ER), androgen receptor (AR), glucocorticoid receptor (GR), progesterone receptor (PR), NFκB, p53, OCT, SOX and PAX. The transcription factor may be a transcription factor identified by sequence analysis or a naturally-occurring reading frame sequence that has not been previously characterized as a transcription factor. The polypeptide may also be an artificially generated or chemically or enzymatically modified polypeptide.

The term "tagged fragments," as used herein, refers to polynucleotide fragments that are attached to tags.

The term "region," as used herein, refers to a contiguous length of nucleotides in a genome of an organism. A chromosomal region may be in the range of 1 bp to the length of an entire chromosome. In some instances, a region may have a length of at least 200 bp, at least 500 bp, at least 1 kb, at least 10 kb or at least 100 kb or more (e.g., up to 1 Mb or 10 Mb or more). The genome may be from any eukaryotic organism, e.g., an animal or plant genome such as the genome of a human, monkey, rat, fish or insect.

The term "epigenetic map," as used herein, refers to any representation of epigenetic features, e.g., sites of nucleosomes, nucleosome-free regions, binding sites for transcription factors, etc. A map can be physically displayed, e.g., on a computer monitor.

The term "mapping information," as used herein, refers to assembling experimentally-obtained information about an area to a physical map of the area.

The term "chromatin accessibility," as used herein, refers to how accessible a nucleic acid site is within a polynucleotide, such as in genomic DNA, i.e., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins).

In one embodiment, the invention provides a method for sequencing at least one target nucleic acid in a fixed and, optionally, expanded biological sample. In an embodiment of the invention, the method comprises the steps: (a) fixing a biological sample; (b) optionally expanding the biological sample, (c) incubating the biological sample with a pair of polynucleotides complementary to non-overlapping and proximal sequences of a target nucleic acid, wherein the polynucleotide pair hybridizes to the target nucleic acid; (d) ligating the polynucleotide pair using a ligase; (e) amplifying the ligation product; and (f) sequencing the amplification product. In one embodiment, the method further comprises the step of (h) localizing the target nucleic acid within the sample. As the method comprises hybridizing polynucleotide pairs to a target nucleic acid in a fixed biological sample, the target nucleic acid can be hybridized in situ. As used herein, the terms "hybridized in situ" or "in situ hybridization" refer to a technique for localizing specific nucleic acid targets within fixed tissues and cells, providing temporal and spatial information about gene expression and genetic loci.

In one embodiment, the invention provides a method for sequencing at least one target nucleic acid in a fixed and, optionally, expanded biological sample. In an embodiment of the invention, the method comprises the steps: (a) incubating the biological sample with a pair of polynucleotides complementary to non-overlapping and proximal sequences of a target nucleic acid, wherein the polynucleotide pair hybridizes to the target nucleic acid; (b) ligating the polynucleotide pair using a ligase; (c) amplifying the ligation product; and (d) sequencing the amplification product. In one embodiment, the method further comprises the step of (e) localizing the target nucleic acid within the sample.

The term "a pair of polynucleotides" refers to two oligonucleotides that have complementary sequences to the target nucleic acid. Each polynucleotide of the pair is also referred to herein as a "target-complementary polynucleotide". In one embodiment, the pair of polynucleotides comprise two independent, linear polynucleotides that are complementary to non-overlapping and proximal sequences of the target nucleic acid. The 5' end of one of the polynucleotides and the 3' end of the other polynucleotide are brought into juxtaposition by hybridization to a target sequence. This juxtaposition allows the two polynucleotides to be covalently joined by the action of a ligase.

In one embodiment, a pair of polynucleotides can refer to a single pair of polynucleotides. In another embodiment, a pair of polynucleotides can refer to a library of polynucleotide pairs, wherein each independent pair comprises two polynucleotides complementary to non-overlapping and proximal sequences of a target nucleic acid. For example, a library of polynucleotides pairs can comprise 2 or more polynucleotide pairs, 10 or more polynucleotide pairs, 100 or more polynucleotide pairs, 1000 or more polynucleotide pairs, 10,000 or more polynucleotide pairs, or more than 20,000 polynucleotide pairs, including any number in between. It is important to note that a polynucleotide pair preferably consists of two polynucleotides. However, it is possible that each "pair" have three or more polynucleotides complementary to non-overlapping and proximal sequences of a target nucleic acid.

The term "complementary to non-overlapping and proximal sequences of the target nucleic acid" refers to a pair of polynucleotides where one polynucleotide is complementary to a sequence of the target nucleic acid and the other polynucleotide(s) is/are complementary to a different sequence of the target nucleic acid, wherein the distance between the ends of the two polynucleotides, also referred to as the "ligation junction," as measured by nucleobases, is preferably less than about 20 nucleobases. In one embodiment, the polynucleotides are from 0 to about 20 nucleobases apart (e.g., the ligation junction is less than 20 nucleobases). In one embodiment, the polynucleotides are from 0 to about 15 nucleobases apart (e.g., the ligation junction is less than 15 nucleobases). In one embodiment, the polynucleotides are from 0 to about 10 nucleobases apart (e.g., the ligation junction is less than 10 nucleobases). In one embodiment, the polynucleotides are from 0 to about 5 nucleobases apart (e.g., the ligation junction is less than 5 nucleobases). In one embodiment, the ligation junction is selected form the group consisting of 0, 1, 2, 3, 4, 5, 6, 7, 8, 9, 10, 11, 12, 13, 14, 15, 16, 17, 18, 19, or 20 nucleobases. In one embodiment, the ligation junction is 0 nucleobase. In a preferred embodiment, the ligation junction is zero and the 5' end of one polynucleotide abuts the 3' end of the other polynucleotide.

The nature of pair of polynucleotides and stringent requirements for ligation make them especially useful for in situ hybridization and detection of a target nucleic acid. In situ hybridization is a technique where the polynucleotides are hybridized with the target nucleic acid sequence that is to be detected, wherein this sequence is present at its original place (in-situ), i.e., within the cell or tissue, thereby aiding in localizing the target sequence.

The polynucleotides can comprise additional sequences that can be used for amplification, for example, primer binding sites, and/or identification via DNA tag or barcode.

Each polynucleotide of the pair of polynucleotides is independently from about 8 to about 100 nucleotides in length. In one embodiment, each polynucleotide is independently from about 8 to about 40 nucleotides long. In one embodiment, each polynucleotide is independently from about 10 to about 100 nucleotides long. In one embodiment, each polynucleotide is independently from about 10 to about 40 nucleotides long. In one embodiment, each polynucleotide is independently from about 8 to about 25 nucleotides long. In one embodiment, each polynucleotide is independently from about 10 to about 25 nucleotides long. In one embodiment, each polynucleotide is independently from about 15 to about 23 nucleotides long. In one embodiment, each polynucleotide is about 16 nucleotides long. In one embodiment, each polynucleotide is the same number of nucleotides in length.

In one embodiment, the pair of polynucleotides are part of a single, linear oligonucleotide comprising the two polynucleotides complementary to non-overlapping and proximal sequences of the target nucleic acid connected by a polynucleotide linker, wherein one of the target-complementary polynucleotides is at the 5' end of the oligonucleotide and the other target-complementary polynucleotide is at the 3' end of the oligonucleotide.

The 5' end and the 3' end of the oligonucleotide are brought into juxtaposition by hybridization to a target sequence, forming a circle above the target. This juxtaposition allows the ends of the oligonucleotide to be covalently joined by the action of a ligase.

The nature of pair of polynucleotides and stringent requirements for ligation make them especially useful for in situ hybridization and detection of a target nucleic acid. In situ hybridization is a technique where the polynucleotides are hybridized with the target nucleic acid sequence that is to be detected, wherein this sequence is present at its original place (in-situ) within the cell or tissue, thereby aiding in localizing the target sequence.

The oligonucleotide can comprise additional sequences that can be used for amplification, for example, primer binding sites, and/or identification via DNA tag or barcode. In one embodiment, these additional sequences are located within the linker sequence.

Each target-complementary polynucleotide of the oligonucleotide is independently from about 8 to about 100 nucleotides in length. In one embodiment, each polynucleotide is independently from about 8 to about 40 nucleotides long. In one embodiment, each polynucleotide is independently from about 10 to about 100 nucleotides long. In one embodiment, each polynucleotide is independently from about 10 to about 40 nucleotides long. In one embodiment, each polynucleotide is independently from about 8 to about 25 nucleotides long. In one embodiment, each polynucleotide is independently from about 10 to about 25 nucleotides long. In one embodiment, each polynucleotide is independently from about 15 to about 23 nucleotides long. In one embodiment, each polynucleotide is about 16 nucleotides long. In one embodiment, each polynucleotide is the same number of nucleotides in length.

The polynucleotide linker can be of any length sufficient to allow both of the target-complementary polynucleotide ends of the oligonucleotide to bind the target sequence. In this respect, the polynucleotide linker is at least as long as the length of the target-complementary polynucleotide ends combined. For example, if the target-complementary polynucleotides are each 8 nucleotides in length then the polynucleotide linker comprises at least 16 nucleotides. In one embodiment, the polynucleotide linker is from about 16 to about 200 nucleotides long. In one embodiment, the polynucleotide linker is from about 20 to about 100 nucleotides long. In one embodiment, the polynucleotide linker is from about 20 to about 60 nucleotides long. In one embodiment, the polynucleotide linker is from about 20 to about 50 nucleotides long. In one embodiment, the polynucleotide linker is about 42 nucleotides long.

The pair of polynucleotides, when exposed to a biological sample, will bind with the target nucleic acid, thereby forming a hybrid. The biological sample is exposed to a ligase and upon recognition of and hybridization to the target nucleic acid by the 5' end of one of the target-complementary polynucleotides and the 3' end of the other target-complementary polynucleotide the polynucleotide pairs are ligated to each other through the action of a ligase. The pair of polynucleotides can hybridize the target with a high index of specificity due to the fact that two arms are required to bind target segments independently, which is subsequently ligated.

Where the pair of polynucleotides comprise two independent linear polynucleotides complementary to adjacent sequences within the target nucleic acid (i.e., the ligation junction is 0), the polynucleotides hybridize to the target nucleic acid and are ligated by a ligase into a single linear polynucleotide. The length of the ligated polynucleotide is equal to the length of the two target-complementary polynucleotides.

Where the pair of polynucleotides comprise two independent linear polynucleotides complementary to proximal but non-adjacent sequences within the target nucleic acid (i.e., the ligation junction gap is about 1-20 nucleotides in length), upon hybridization of the polynucleotides to the target nucleic acid the gap between the polynucleotides must be filled prior ligation by the ligase. The gap can be filled by any method known to one skilled in the art, for example, but not limited to, using a DNA polymerase such as a Reverse transcriptase and free nucleotides to fill the gap. Once the gap is filled, the ends of the polynucleotides are ligated by a ligase into a single linear polynucleotide. The length of the ligated polynucleotide is equal to the length of the two target-complementary polynucleotides plus the number of nucleotides required to fill the gap.

Where the pair of polynucleotides are part of a single, linear oligonucleotide comprising the two target-complementary polynucleotides connected by a polynucleotide linker, both ends of the oligonucleotide hybridize with the target DNA sequence facing each other, forming a circular structure. In the presence of a DNA ligase, the ends of the oligonucleotide are ligated, thus, a circular closed structure is formed above the target nucleic acid. Where the pair of polynucleotides are complementary to adjacent sequences within the target nucleic acid (i.e., the ligation junction is 0), the polynucleotides hybridize to the target nucleic acid and are ligated by a ligase into a single, circular oligonucleotide. The length of the ligated polynucleotide is equal to the length of the oligonucleotide.

Where the pair of polynucleotides are complementary to proximal but non-adjacent sequences within the target nucleic acid (i.e., the ligation junction gap is about 1-20 nucleotides in length), upon hybridization of the polynucleotides to the target nucleic acid the gap between the polynucleotides must be filled prior ligation by the ligase. The gap can be filled by any method known to one skilled in the art, for example, but not limited to, using a DNA polymerase such as a Reverse transcriptase and free nucleotides to fill the gap. Once the gap is filled, the ends of the polynucleotides are ligated by a ligase into a single, circular oligonucleotide. The length of the ligated oligonucleotide is equal to the length of the oligonucleotides plus the number of nucleotides required to fill the gap.

The nature of the pair of polynucleotides and stringent requirements for ligation are especially useful for in-situ hybridization. In-situ hybridization is a technique where the probe is hybridized with the target DNA or RNA sequence that is to be detected, wherein the sequence is present at its original place (in-situ), i.e., within the cell, tissue sections, thereby aiding in localizing the target sequence at its original place.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide.

A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) Nucl. Acids Res. 27:875; Higgins et al., Meth. in Enzymol. (1979) 68:50; Engler et al. (1982) The Enzymes, 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include SplintR ligase, T4 DNA ligase, T7 DNA ligase, E. coli DNA ligase, Taq ligase, Pfu ligase and the like. Certain protocols for using ligases are disclosed by the manufacturer and also in Sambrook, Molecular Cloning: A Laboratory manual, 2.sup.nd Edition (Cold Spring Harbor Laboratory, New York, 1989); barany, PCR Methods and Applications, 1:5-16 (1991); Marsh et al., Strategies, 5:73-76 (1992). In one embodiment, the ligase may be derived from algal viruses such as the Chlorella virus, for example, PBCV-1 ligase, also known as SplintR ligase, as described US Patent Publication No. 2014/0179539, incorporated herein by reference in its entirety.

The expression "amplification" or "amplifying" refers to a process by which extra or multiple copies of a particular polynucleotide are formed. The term "amplification product" refers to the nucleic acids, which are produced from the amplifying process as defined herein.

Amplification includes methods generally known to one skilled in the art such as, but not limited to, PCR, ligation amplification (or ligase chain reaction, LCR), real time (rtPCR) or quantitative PCR (qPCR), rolling circle amplification (RCA), and other amplification methods. These methods are generally known. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In one embodiment, the ligation product is amplified using PCR. In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. In one embodiment, the ligation product is amplified using qPCR. Quantitative polymerase chain reaction is used to simultaneously detect a specific DNA sequence in a sample and determine the actual copy number of this sequence relative to a standard. In one embodiment, the ligation product is amplified using rtPCR. In real-time PCR, the DNA copy number can be established after each cycle of amplification. By using a fluorescent reporter in the reaction, it is possible to measure DNA generation.

OTHER APPLICATIONS OF THE INVENTION

In addition to RNAs and DNAs, proteins, amino acid motifs, macromolecular complexes, and atomic configurations may be detected in situ using antigen-binding epitopes. These epitopes may be modified with a label for identification (such as a DNA barcode or fluorophore) as well as a methacryl group for co-polymerization with the expanding gel. Antigen-binding epitopes include antibodies, proteins, small molecules, and aptamers.

The present invention will be better understood in connection with the following Examples. However, it should be understood that these examples are for illustrative purposes only and are not meant to limit the scope of the invention. Various changes and modifications will be apparent to those skilled in the art and such changes and modifications including, without limitation, those relating to the formulations and/or methods of the invention may be made without departing from the spirit of the invention and the scope of the appended claims.

EXAMPLES

Figure 2:
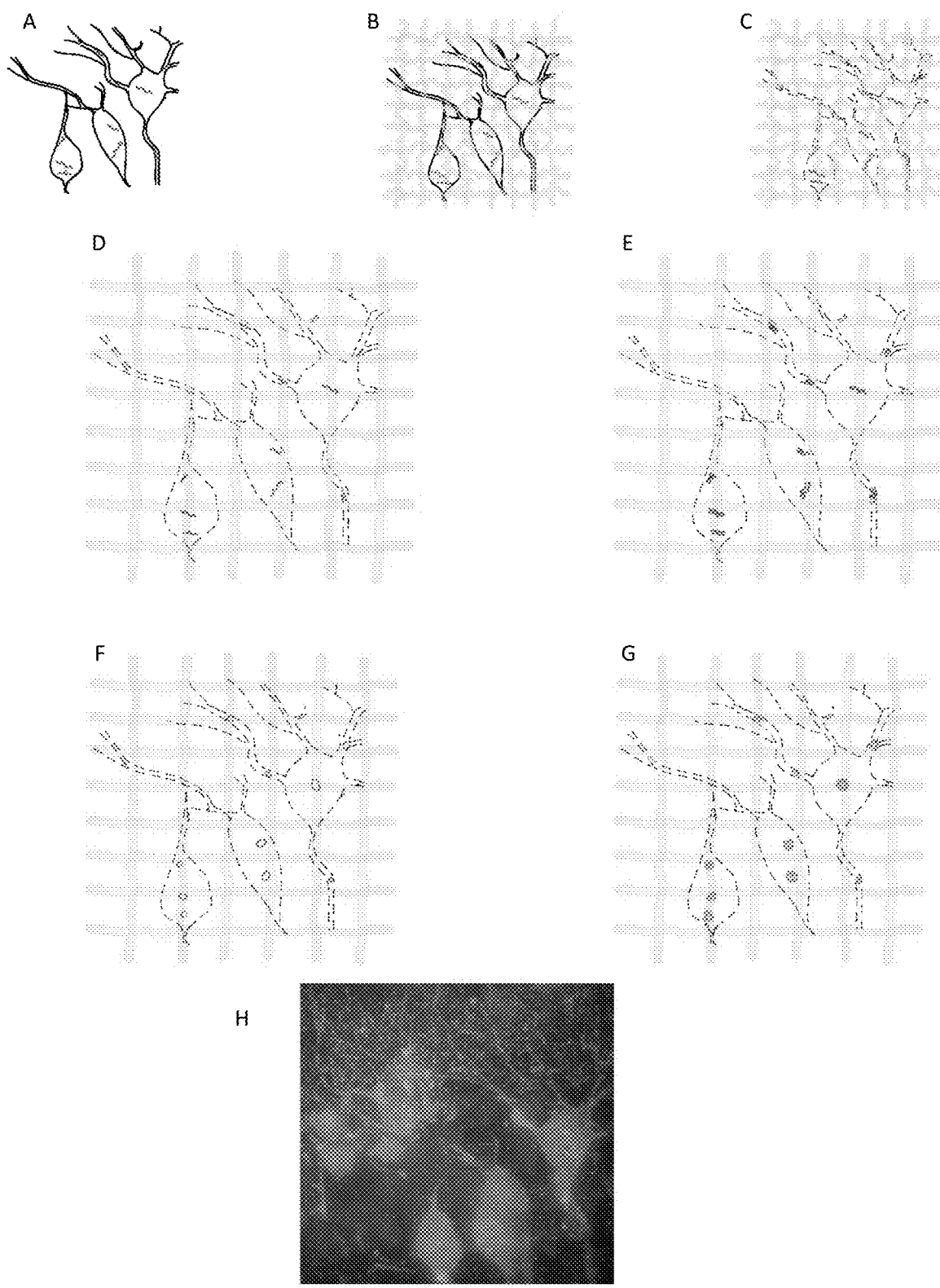
FIG. 2. Schematic showing in situ expansion sequencing conducted on biological samples that have been physically expanded: Panel A depicts that the RNA molecules are tagged; Panel B depicts that biological specimens are embedded in a swellable gel material; Panel C depicts disruption of the native biological networks; Panel D depicts expansion of the sample and that the tagged RNA molecules are incorporated into the swellable material; Panel E depicts using the FISSEQ method, RNA molecules present in the sample are reverse transcribed to cDNA; Panel F depicts that RNA molecules are circularized using CircLigase; Panel G depicts RNA amplified using rolling circle amplification; Panel H depicts amplified cDNA (green) in expanded mouse hippocampus. Thy1-YFP mice were used, thereby allowing sparse neuronal labeling (red); the nuclei are DAPI-stained (blue); the amplified cDNA can now be sequenced in situ using sequencing by ligation.
Figure 3:
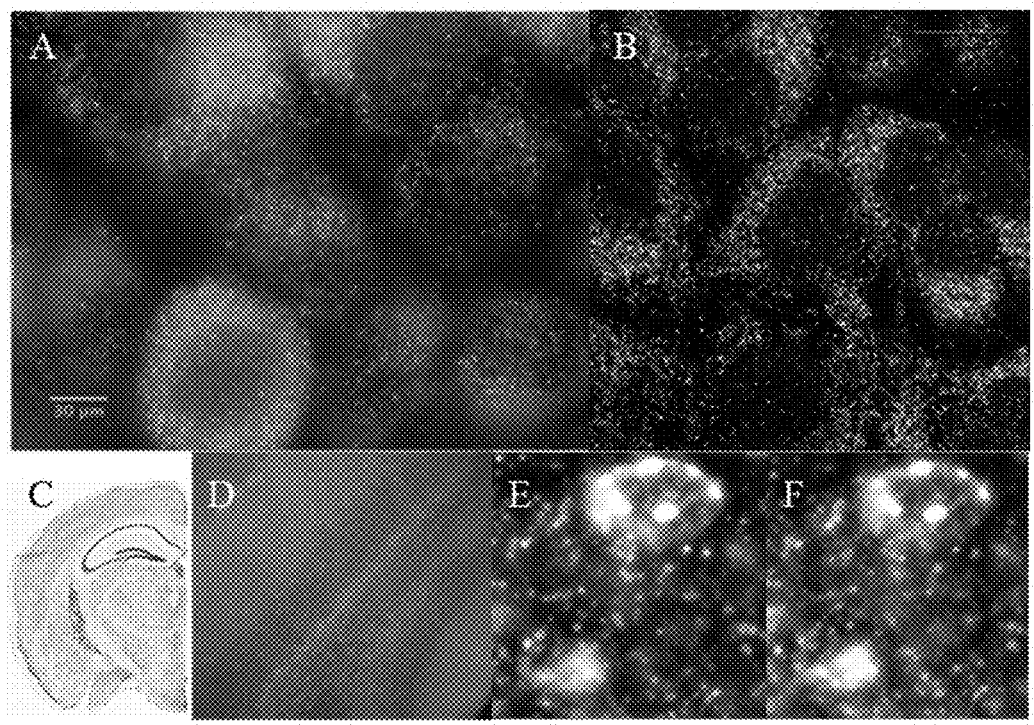
FIG. 3. Microscopy images showing in situ sequencing in expanded human cell line and expanded mouse brain tissue are shown. Panels A and D show amplified cDNA (green) in expanded human HeLa cell line (Panel A) and expanded mouse hippocampus (Panel D). The nuclei are DAPI-stained (blue). Panel C is a section of the mouse brain showing the hippocampus (from Allen Brain Atlas). Panels B, E and F show sequencing by ligation in expanded human HeLa cell line (Panel B) and expanded mouse hippocampus (Panels E and F). In each sequencing round different colors (blue, magenta, green, and red) reveal the current base of the amplified cDNA. Overall, 32 bases were sequenced from each amplified cDNA in the region of the expanded mouse hippocampus shown in (Panel D). Panel E shows sequencing of a region from the sample in Panel D. Panel F shows the next base of the sample from Panel E being sequenced.

Demonstration of ExSEQ:

To demonstrate ExSEQ, we have expanded human HeLa cell lines and a slice of mouse hippocampus and generated libraries of cDNA amplicons using the chemical RNA capture strategy (FIG. 2 and FIG. 3). Next, we sequenced 32 bases of the cDNA amplicons in expanded mouse hippocampus in situ (FIG. 3). As expected, most of the cDNA mapped to the correct annotated strand of known mRNA. Importantly, the highly expressed cDNA mapped to known neuronal genes, including neurotransmitter transporters, channels, and receptors. The yield obtained and the sequence identities of the cDNA provide evidence that ExSEQ can indeed quantify the transcriptome in expanded tissues in situ.

Brief materials and methods used to create the data described in FIGS. 2 and 3: for the mouse hippocampus data, Thy1-YFP (Tg(Thy1-YFP)16Jrs) male mice in the age range 6-8 weeks were anesthetized with isoflurane and perfused transcardially with ice cold 4% paraformaldehyde. Brains were dissected out, left in 4% paraformaldehyde at 4° C. for one day, before moving to PBS containing 100 mM glycine. 50 m slices were sliced on a vibratome (Leica VT1000S) and stored at 4° C. in PBS until use. The slices were permeabilized in 0.25% Triton X-100 in PBS for 1 hour. For the HeLa (ATCC CCL-2) cell line data, the cells were cultured in Culturewell Chambered Coverglass (Invitrogen), fixed using 10% formalin in PBS for 15 min, and permeabilized in 0.25% Triton X-100 in PBS for 10 minutes.

To obtain the YFP labeling in FIG. 2, the brain samples were stained as in Chen et al., Science, 347, 543 (2015), that is, with primary antibody against GFP (Abcam, ab13970), followed by DNA-labeled secondary antibody, and finally with tri-functional label.

The small chemical LABEL-IT® Amine (Mirus Bio LLC), modified with hydrogel anchorable group (acryloyl-X), was used for RNA capturing. First, 1 mg/mL acryloyl-X was reacted with 1 mg/mL of LABEL-IT® Amine overnight at room temperature with shaking. Next, the samples were incubated with 0.02 mg/mL acryloyl-X-reacted Label-IT in 20 mM MOPS buffer pH 7.7 at 37° C. overnight.

Hydrogel embedding, proteolysis, and expansion were performed as in Chen et al., Science, 347, 543 (2015).

To re-embed the samples in a non-swellable polymer, gels were incubated in 3% acrylamide, 0.15% N,N'-Methylenebisacrylamide with 0.075% APS, 0.075% TEMED and 5 mM Tris ph 10.5 for 20 minutes on a shaker. The gels were then placed in a humidified chamber that was purged with nitrogen gas. Finally, the gels were moved to a 37° C. incubator for gelation for 1.5 hours.

The swellable gel was then passivated by treating the samples with 1-Ethyl-3-(3-dimethylaminopropyl)carbodiimide (EDC) and N-Hydroxysuccinimide (NHS) to covalently react ethanolamine to the carboxylic groups. First, the gels were incubated with 2M Ethanolamine hydrochloride, 150 mM EDC, 150 mM NHS, and 100 mM 2-(N-morpholino)ethanesulfonic acid (MES) buffer ph 6.5 for 2 hours. Next, the gels were incubated with 2M Ethanolamine hydrochloride and 62 mM Sodium borate (SB) buffer at pH 8.5 for 40 minutes.

In Situ Sequencing

Library preparation and nucleic acid sequencing, starting from reverse transcription, were performed as in Lee et al., Science. 343, 1360-3 (2014).

Incorporation mix ("IMT") was extracted from the cartridges of, respectively, a MiSeq Reagent Kit v3 and a NextSeq 500/550 Reagent Kit v2, aliquoted, and frozen. Four template oligonucleotides (see Table 1, each with a unique base downstream of a primer binding site) were individually annealed with primer at a concentration of 45 uM in 1× Annealing Buffer (1x TE pH 7.5, 50 mM NaCl) in a thermal cycler. The annealing involved a 3 minute hold at 95 degrees followed by a −0.1° C. ramp to 25° C. 500 pmol of each of the template-primer duplexes were separately diluted 1:10 into MiSeq and NextSeq IMT. The dilutions were heated at 65° C. for 5 minutes, and then eluted in 20 uL of water using a DNA oligonucleotide clean and concentrate kit (Zymo). The elutant from each reaction was added to a well of a 384-well glass bottom plate, and the absorption and emission spectra were measured using a spectrophotometer.

TABLE 1

Oligonucleotides used in spectral characterization

| Oligonucleotide | Sequence |
| --- | --- |
| Template (A) | GTACTGAACTGTCTCTTATACACATCTGACGCT GCCGACGA (SEQ ID: 1) |
| Template (T) | GTACTGTTCTGTCTCTTATACACATCTGACGCT GCCGACGA (SEQ ID: 2) |
| Template (C) | GTACTGCCCTGTCTCTTATACACATCTGACGCT GCCGACGA (SEQ ID: 3) |

TABLE 1 -continued

Oligonucleotides used in spectral characterization

| Oligonucleotide | Sequence |
|---|---|
| Template (G) | GTACTGGGCTGTCTCTTATACACATCTGACGCT GCCGACGA (SEQ ID: 4) |
| Primer | TCGTCGGCAGCGTCAGATGTGTATAAGAGACAG (SEQ ID: 5) |

Base-specific DNA template-primer duplexes were prepared and, following a single base of synthesis using MiSeq or NextSeq kit-specific fluorescent incorporation mix, the templates were physically isolated from unreacted dyes, and their emission and absorption spectra were measured via spectrophotometry.

Figure 4A:
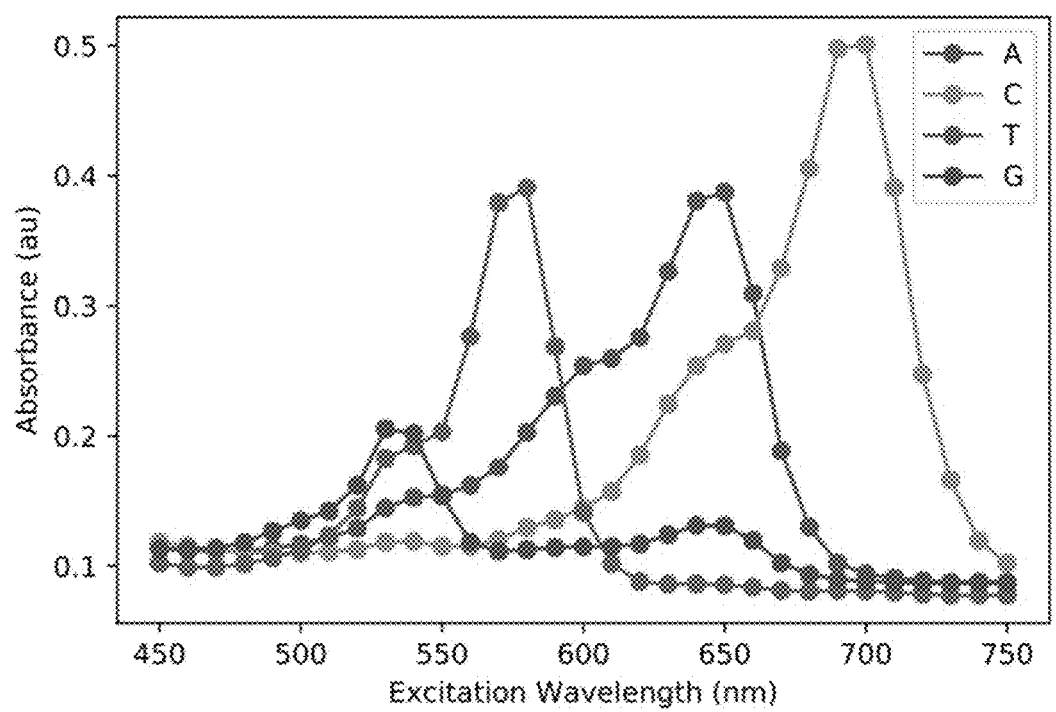
FIG. 4(a) and FIG. 4(b). Measurement of emission and absorption spectra for MiSeq dyes. (a) Absorption spectra for MiSeq dyes indicating four unique colors. (b) Emission spectra for an excitation close to each of the absorption maxima.
Figure 4B:
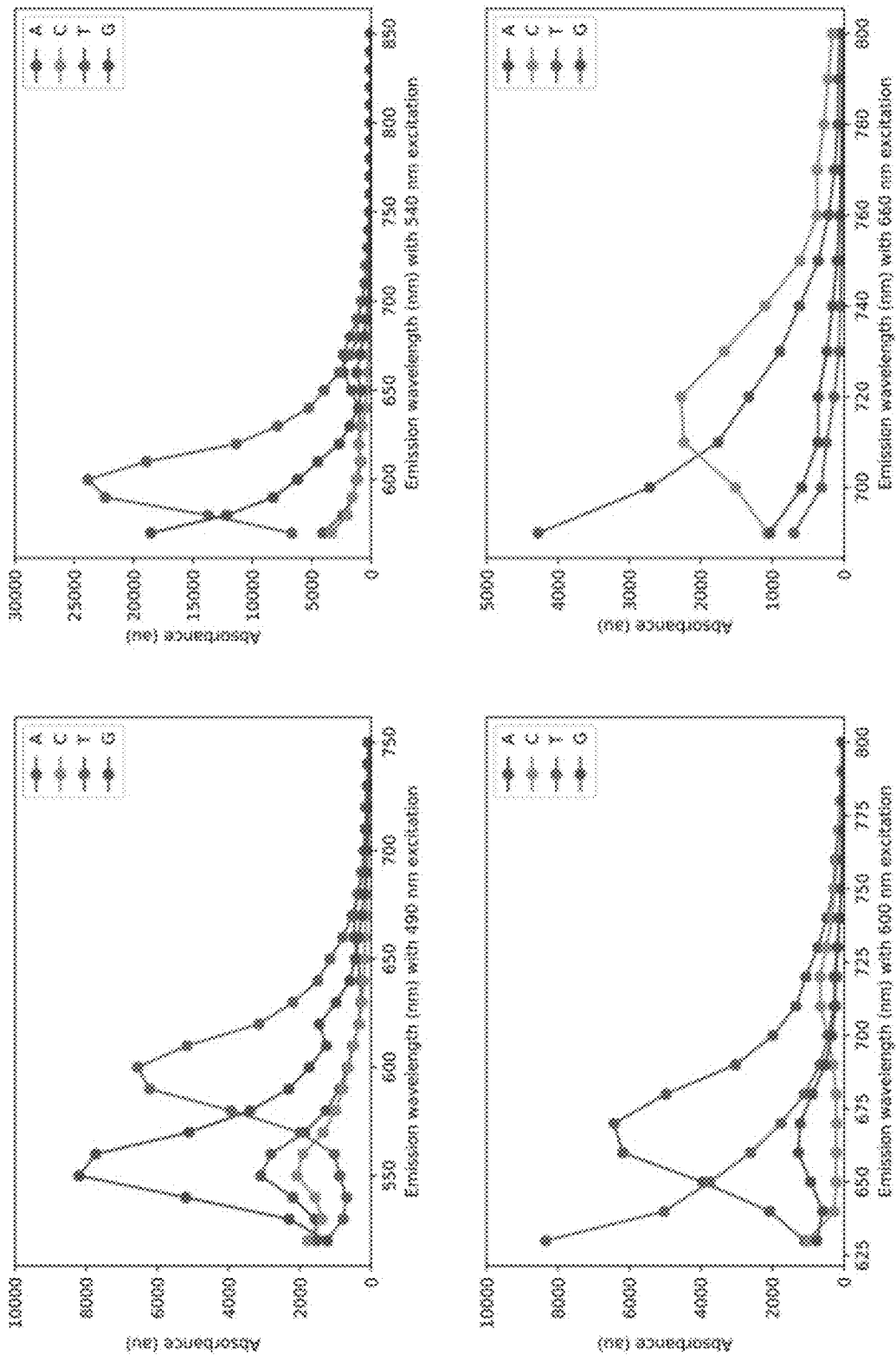

The MiSeq absorption spectra is presented in FIG. 4. There are distinct absorbance maxima for dTTP at 580 nm, dATP at 650 nm, and dCTP at 700 nm. dGTP has two absorbance maxima: a larger one at 530 nm and a smaller one at 640 nm, although it should be noted that both of these maxima are small compared to the maxima for the other three fluorescent dNTPs. In order to relate the absorption maxima to emission spectra, a full spectrum measurement emission measurement was collected for each sample when excited 20-30 nm away from an absorption maximum. There are distinct emission maxima for dGTP at 550 nm, dTTP at 600 nm, dATP at 670 nm, and dCTP at 720 nm.

The NextSeq absorption spectra is presented in FIG. 4. There are distinct absorbance maxima for dTTP at 560 nm, dCTP at 650 nm. dATP has two absorbance maxima of roughly equal intensity at 530 nm and at 660 nm. dGTP has two small absorbance maxima at similar locations to dATP. A similar approach to the last section was used to measure the emission spectra of these samples. There are distinct emission maxima for dATP at 550 nm and 680 nm, dTTP at 580 nm, and dCTP at 670 nm. dGTP can be considered effectively dark when compared to the other three dyes. The results from the spectral measurements are summarized in two tables, Table 2 and Table 3.

TABLE 2

Summary of MiSeq spectral measurements

| Fluorescent dNTP | Absorbance Maximum (nm) | Emission Maximum (nm) |
|---|---|---|
| dGTP | 530 | 550 |
| dTTP | 580 | 600 |
| dATP | 650 | 670 |
| dCTP | 700 | 720 |

TABLE 3

Summary of NextSeq spectral measurements

| Fluorescent dNTP | Absorbance Maximum (nm) | Emission Maximum (nm) |
|---|---|---|
| dGTP | Effectively dark | Effectively dark |
| dTTP | 560 | 580 |
| dATP | 650 | 670 |
| dCTP | 530 and 660 | 550d 680 |

Having obtained spectra for all colors in each of the MiSeq and NextSeq kits a biological sequence can be attributed to a sequence of colors observed under a conventional fluorescence microscope. The ability to attribute a base ("base call") to a cluster depends on both the fidelity of the sequencing chemistry as well as the properties of the lasers and filters used in a particular microscope.

FISSEQ-like in situ RNA sequencing libraries were prepared in hydrogel embedded and expanded rat neuron culture.

Incorporation mix ("IMT"), scan mix ("USM") and cleavage mix ("CMS") were extracted from the cartridges of a MiSeq Reagent Kit v3, aliquoted, and frozen. To perform the sequencing reaction, a sample of RNA sequencing library prepared hydrogel (approximately 3 microliters in volume) was washed twice with 300 uL (i.e. 100× sample volume) of PR2 buffer (supplied with MiSeq kit) for five minutes each. The sample was next immersed in 300 uL IMT, held at 4 C for 10 minutes, then held at 65 C for 30 minutes to incorporate one base of fluorescent dNTP into the library. The sample was then washed twice for 30 minutes with 300 uL of PR2 buffer and then exchanged into 300 uL of USM for imaging. Describe confocal microscope here. Following imaging, the sample was washed twice for 5 minutes with 300 uL of PR2 buffer and exchanged into 300 uL of CMS for 30 minutes at room temperature for cleavage. This process was completed five times to generate five successive image stacks of the region of interest.

To analyze the data, a maximum intensity projection was first performed for each image stack, and each projection was then separated into three images corresponding to each of the imaging channels. For each of these images, maxima coordinates were extracted using the Find Maxima process with manual noise thresholding, generating lists of maxima for each of the three channels for each of the rounds of sequencing.

Using a Python script, intensity tuples were generated from these maxima coordinates. Briefly, for each maximum in a particular channel, an intensity tuple was generated corresponding to the local intensity of that maximum in each of the three channels (rather than just the channel it was detected in), where local intensity is defined as the average of the 3×3 pixel neighborhood centered on the maximum. The local intensities for an individual channel are exponentially distributed; the three distributions were normalized to the intensity of the dimmest channel (here, the 488 nm channel) by scaling the means of the distributions. The normalized intensity tuples for each of the maxima detected in the 488 nm channel and the 560 nm channel were used to generate the crosstalk plots. Pearson's r was computed using for each plot by first aggregating the two sets of intensity tuples and then using the SciPy library of the same name. The fraction of spots passing the threshold intensity was computed as described below.

Sequencing by synthesis on an RNA sequencing library generated in situ was demonstrated. A series of five successive sequencing reactions were performed in situ using reagents extracted from reagent cartridges supplied with a commercially-available Illumina MiSeq kit. The cells were fixed and subsequently embedded in an swellable hydrogel as described herein, providing enhanced resolution and generating a quasi-in-vitro environment in which enzymatic reactions can occur. The sequencing library itself was prepared according to a method similar to FISSEQ (i.e., the nucleic acid clusters are prepared via randomly primed reverse transcription, followed by circularization and phi29-mediated rolling circle amplification).

Figure 5A:
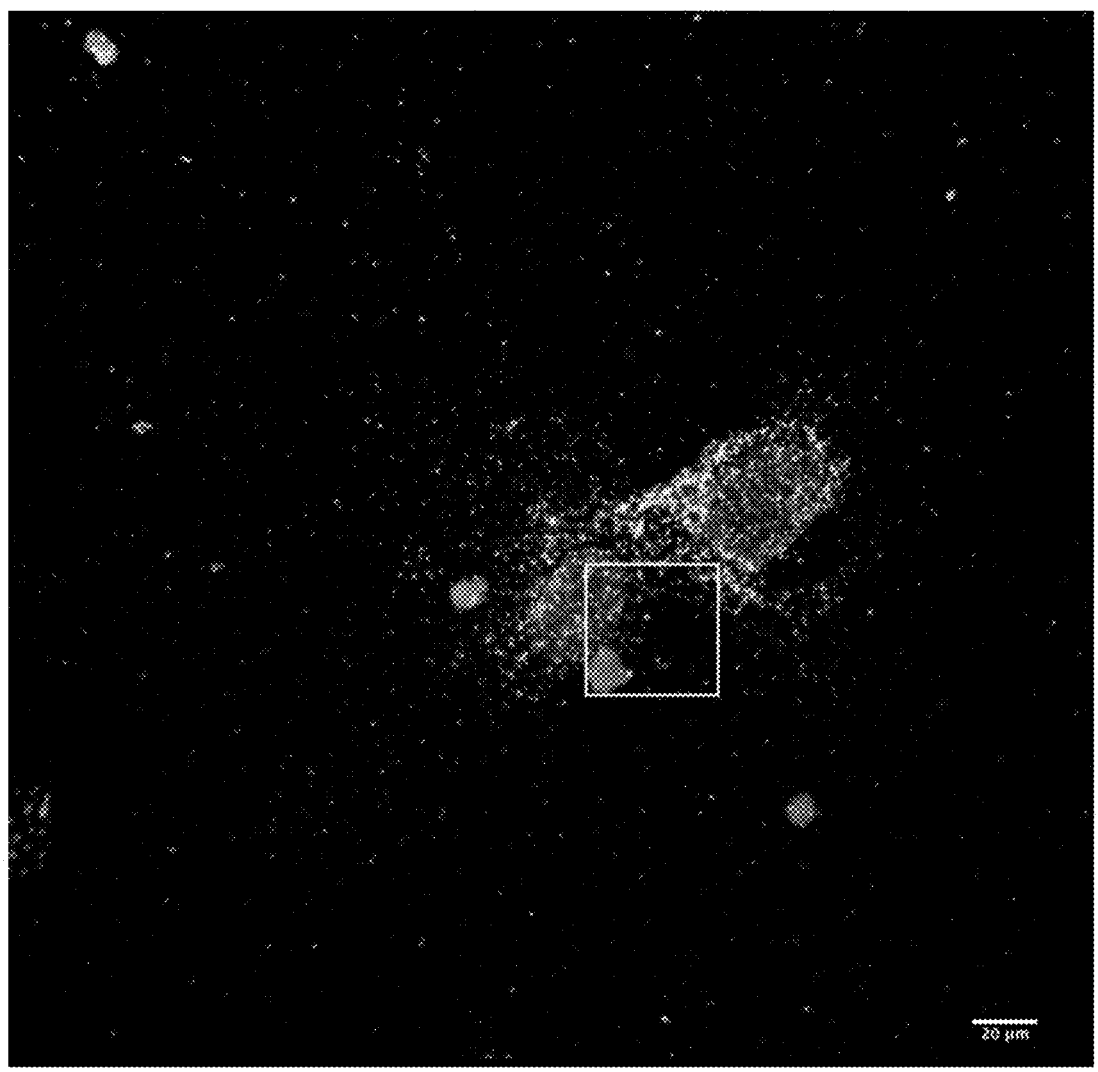
FIG. 5(a) and FIG. 5(b). Demonstration of sequencing by synthesis in situ. (a) Representative region of interest of an initial base of sequencing of an RNA sequencing library prepared in an expanded sample. (b) Multiple bases of sequencing by synthesis. Individual clusters change color from round-to-round.
Figure 5B:
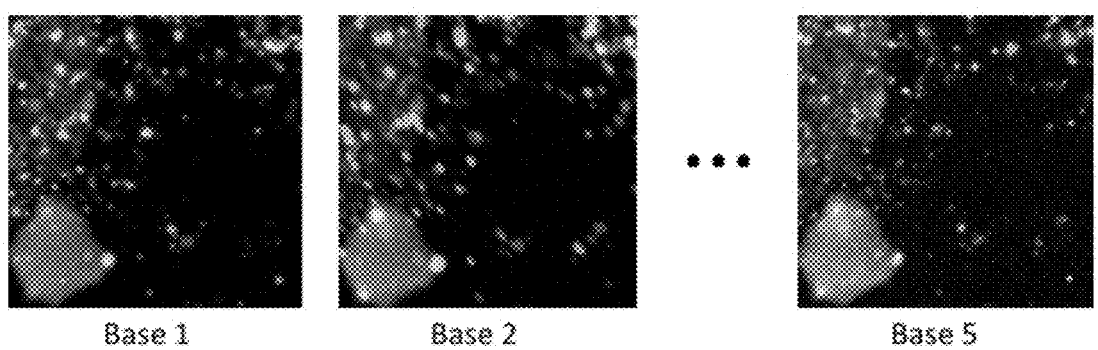

A representative region of interest (ROI) from the sequenced sample, after the first base of sequencing, is shown in FIG. 5(a). Visual inspection indicates that individual clusters correspond to one particular color (they are "clonal") rather than a blend of colors ("polyclonal"). Individual clusters also change color from round-to-round, as expected; this is illustrated in FIG. 5(b).

There are four dye colors in a MiSeq kit; however, due to constraints on the lasers and filters available, all four bases were not imaged independently. The dye corresponding to G can be imaged independently using a standard 488 nm channel, and the dye corresponding to T can be imaged independently using a 560 nm channel; however, the dyes corresponding to A and C are both excited and visible using a 640 nm channel. This can be corroborated by examining the number of maxima in each channel detected for the ROI. This degeneracy introduces ambiguity in sequence reconstruction; however, the performance of the sequencing reactions themselves in situ, and in particular with round-to-round phasing, can proceed by only examining the 488 nm and 560 nm channels, since, as demonstrated, only two independent channels are required for this purpose.

Figure 6:
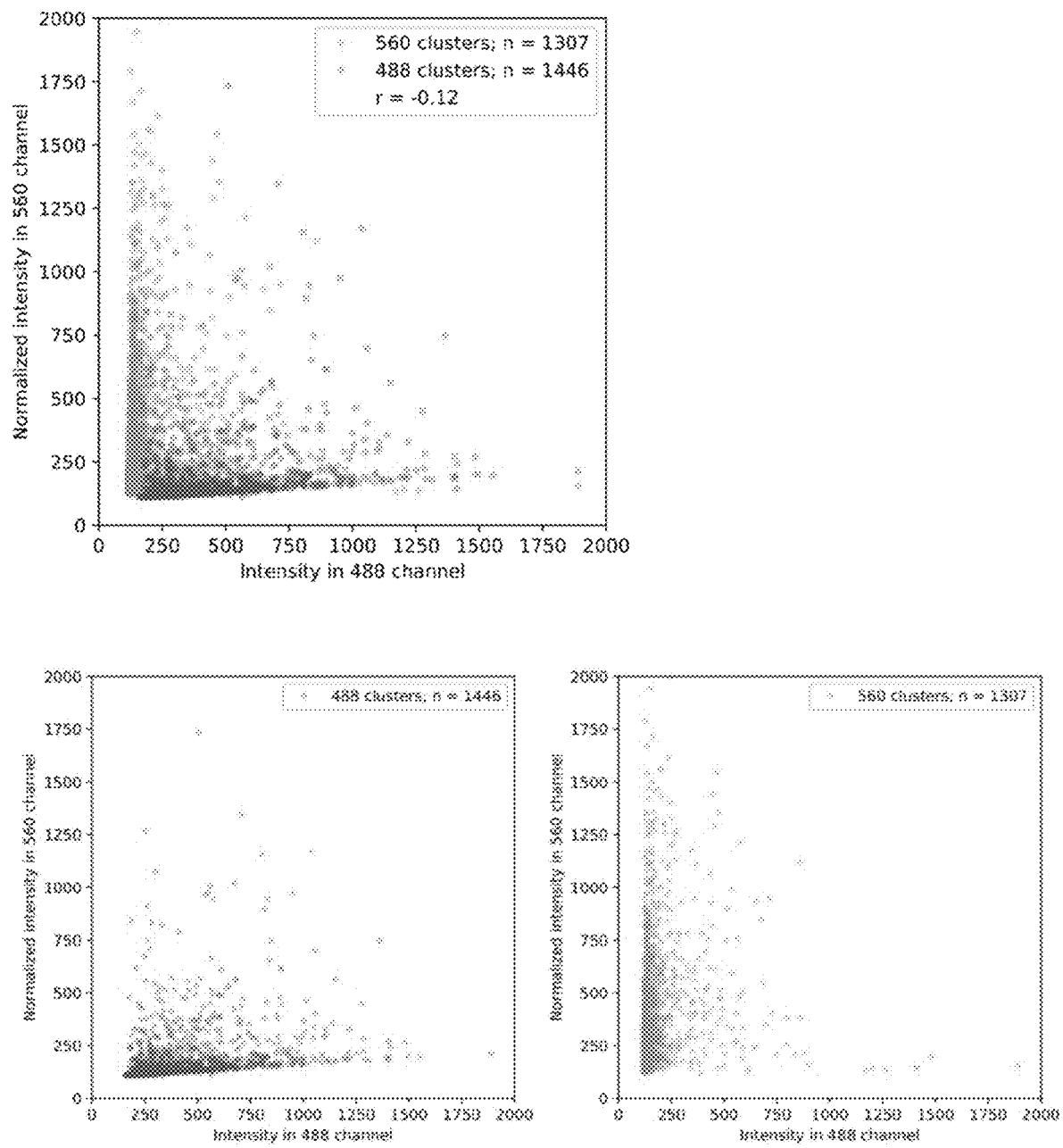
FIG. 6. Intensity crosstalk plot for the first base of sequencing for clusters detected in the 488 nm channel ("G") and the 560 nm channel ("T"). The clusters separate into two distinct, roughly orthogonal components, and the aggregate dataset shows low correlation, both indicative of highly clonal clusters.

In order to quantify the phasing, the images were processed in order to generate pairs of cluster intensities; that is, for each cluster identified as a maximum in the 488 channel or the 560 channel, the intensities of that cluster in both the 488 and 560 channels were extracted. The pairs of intensities for all clusters (i.e. identified in either channel), for the first base of sequencing, are plotted in aggregate as a crosstalk plot in FIG. 6, with a color assigned to each set of clusters as a guide to the eye.

Figure 7:
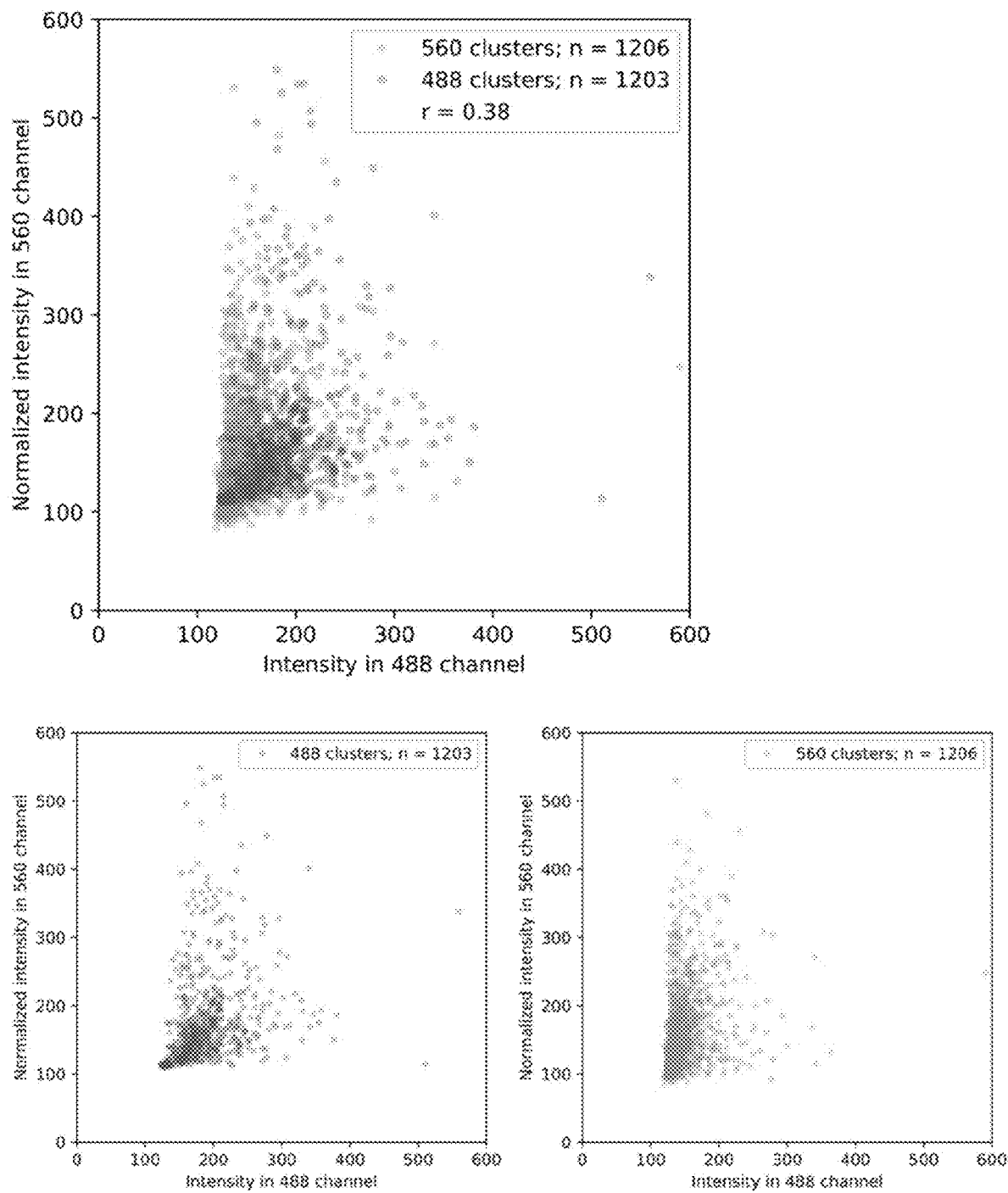
FIG. 7. Intensity crosstalk plot for the fifth base of sequencing. The clusters have become significantly dimmer and more correlated, indicating incomplete addition and an increase in polyclonality.

A "perfect" dataset would be composed of two perfectly orthogonal components (i.e., every dye cluster is monoclonal), however any real cluster will have some degree of crosstalk due to chemistry errors, noise, or experimental biases (i.e., excitation crosstalk). It is clear from visual inspection of FIG. 6 that there are two approximately orthogonal components corresponding to monoclonal clusters, with a smaller set of polyclonal clusters falling between the two arms of the crosstalk plot. The cluster polyclonality increases over multiple sequencing rounds: FIG. 7 plots the cluster crosstalk for the fifth round of sequencing, where the two components are highly correlated and difficult to visually distinguish.

Figure 8:
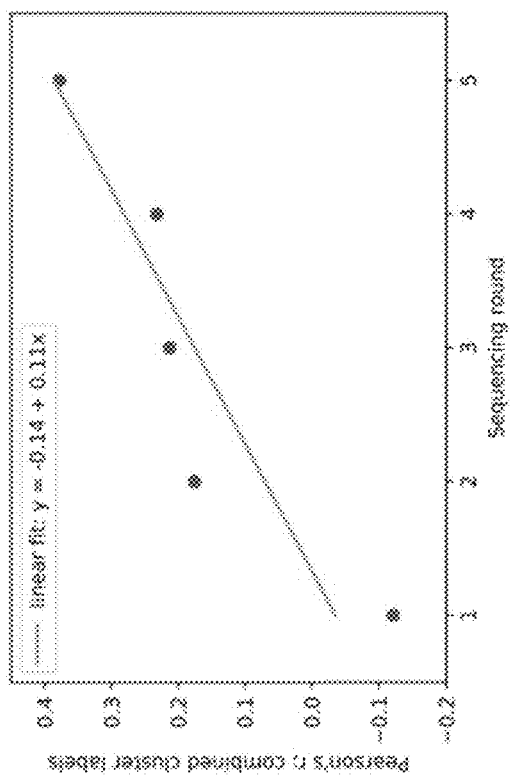
FIG. 8. Crosstalk plot correlation over multiple sequencing rounds. The correlation increases monotonically and roughly linearly, indicating a steady accumulation of chemistry errors (phasing).
Figure 8:
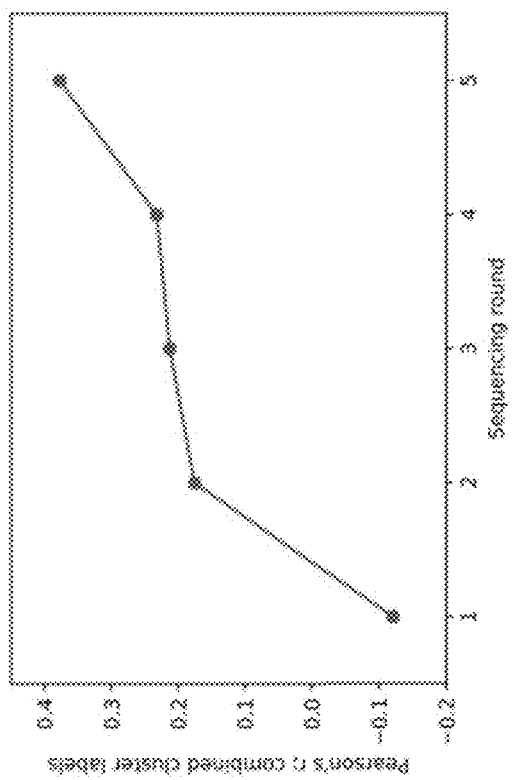

One facile method to quantify the cluster crosstalk over sequencing cycles is to compute Pearson's correlation coefficient (r) for both components in aggregate: as the two arms of the crosstalk plot become less orthogonal due to phasing, they are necessarily more correlated. As see in FIG. 8 that r increases monotonically and roughly linearly with successive rounds of sequencing.

Figure 9:
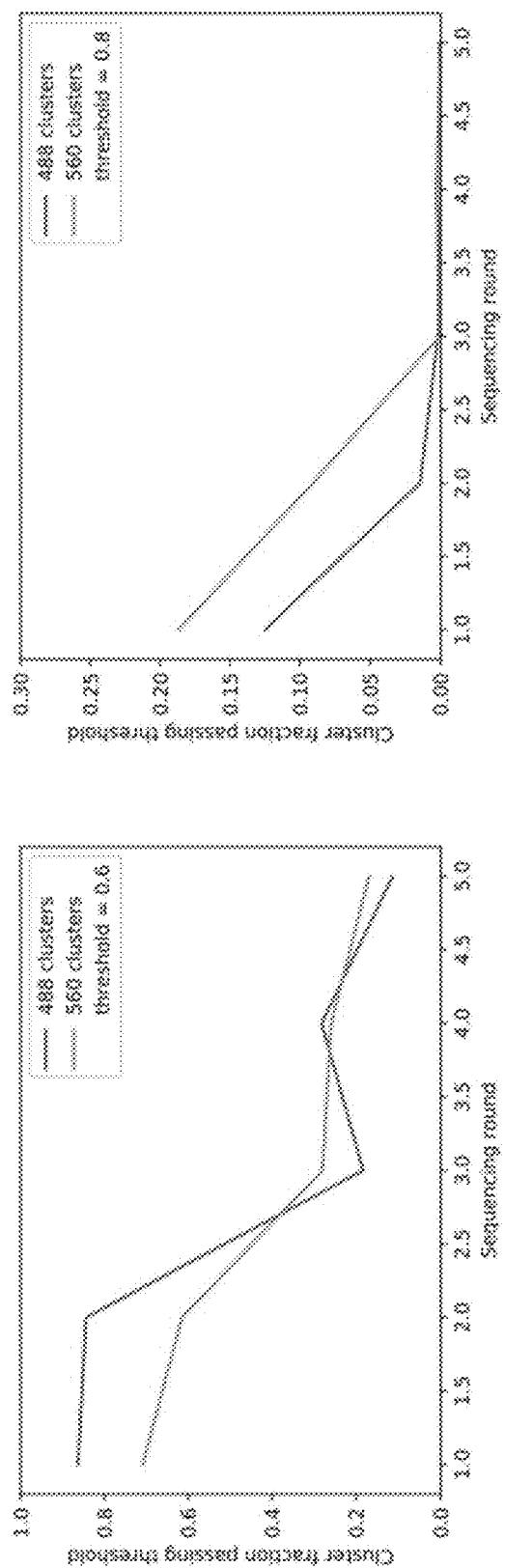
FIG. 9. Analysis of phasing on a per-cluster basis, showing the fraction of clusters that are sufficiently clonal to pass an intensity threshold (i.e., a "chastity filter").

The crosstalk correlation is useful but incomplete metric, since individual clusters may still be "callable" if one color remains dominant. To explore this possibility a second, threshold intensity based metric similar to the CHASTITY metric used in certain base calling methods was defined. A threshold intensity is defined as:

$$I_T = \frac{I_{highest\ channel}}{I_{highest\ channel} + I_{second\ highest\ channel}}$$

and compute $I_T$ for each cluster in the crosstalk plot (there are, of course, only two channels). The fraction of all clusters passing the threshold for two different representative thresholds in FIG. 9 were plotted, where a threshold of 0.6 is typical. A majority of clusters pass this threshold for the first and second rounds of sequencing, but the quality declines rapidly thereafter; this effect is even more pronounced for a threshold of 0.8.

A naive use of MiSeq reagents in this in situ context permits identification of the first few bases of a cluster, but the sequencing fidelity falls rapidly with successive rounds of sequencing. This is attributable to a high degree of round-to-round phasing, as demonstrated by the steady increase in correlation between the two intensity components of each cluster. These results suggest that optimizations increasing the yield and fidelity of the MiSeq sequencing reaction would be desirable in order to generate long, biologically meaningful reads.

Methods were performed as described above, with the sole exception of the IMT incubation step being repeated before each round of imaging.

Figure 10:
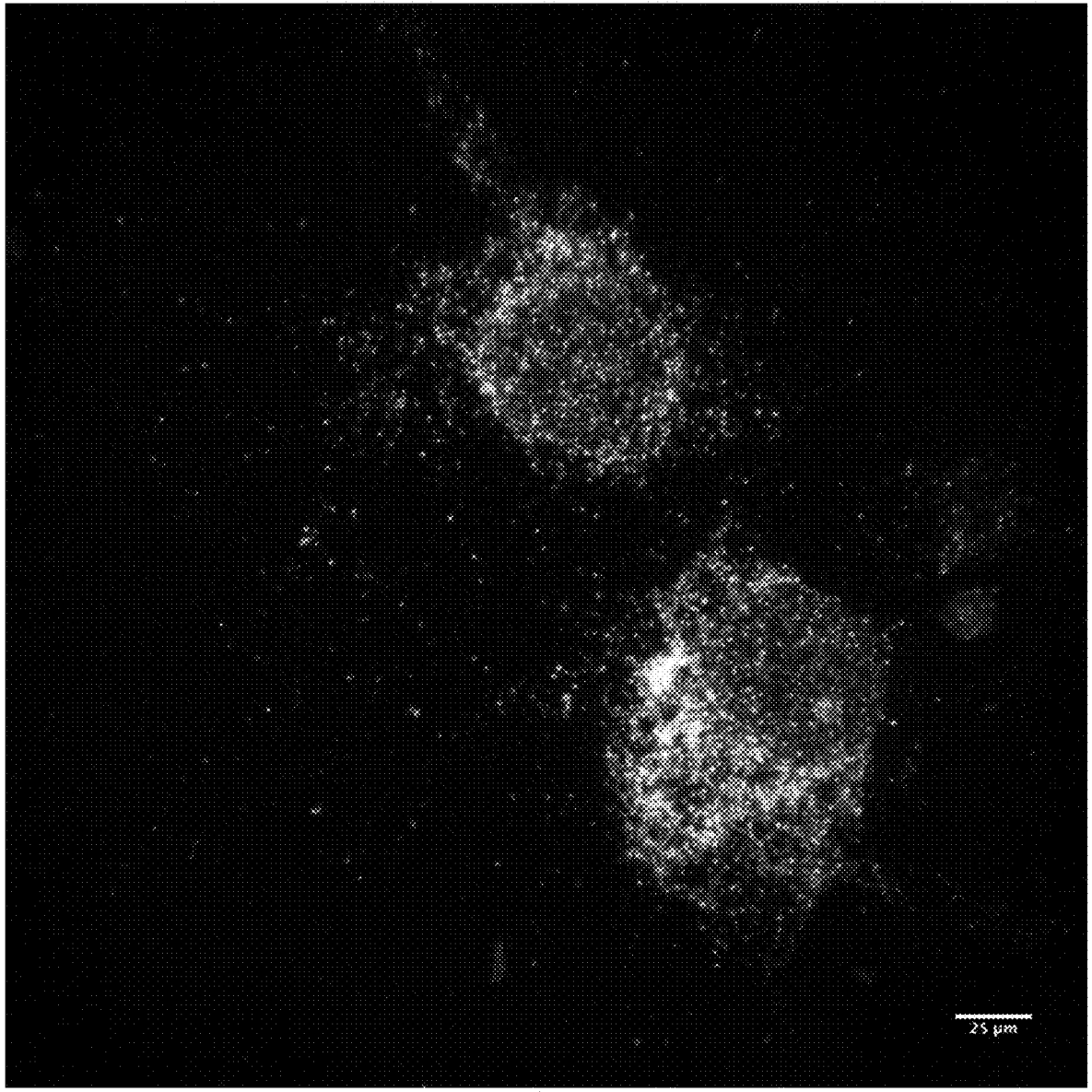
FIG. 10. Representative region of interest of an initial base of sequencing of an RNA sequencing library prepared in an expanded sample, with two rounds of synthesis before imaging.
Figure 11:
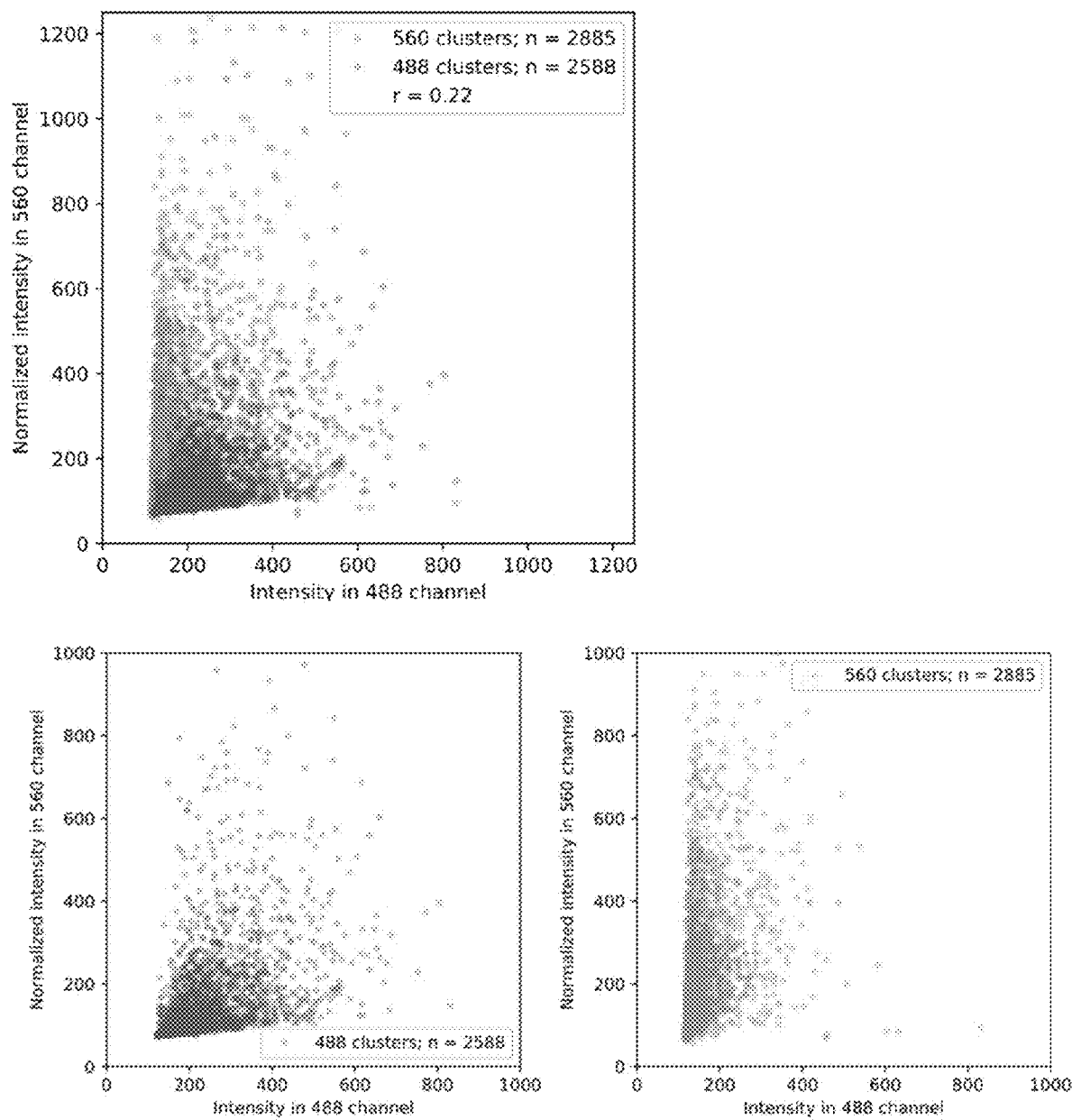
FIG. 11. Crosstalk plot for the first base of sequencing, with two rounds of synthesis before imaging. The two channels are more correlated initially than in the analogous case for one round of synthesis (see FIG. 6).
Figure 12:
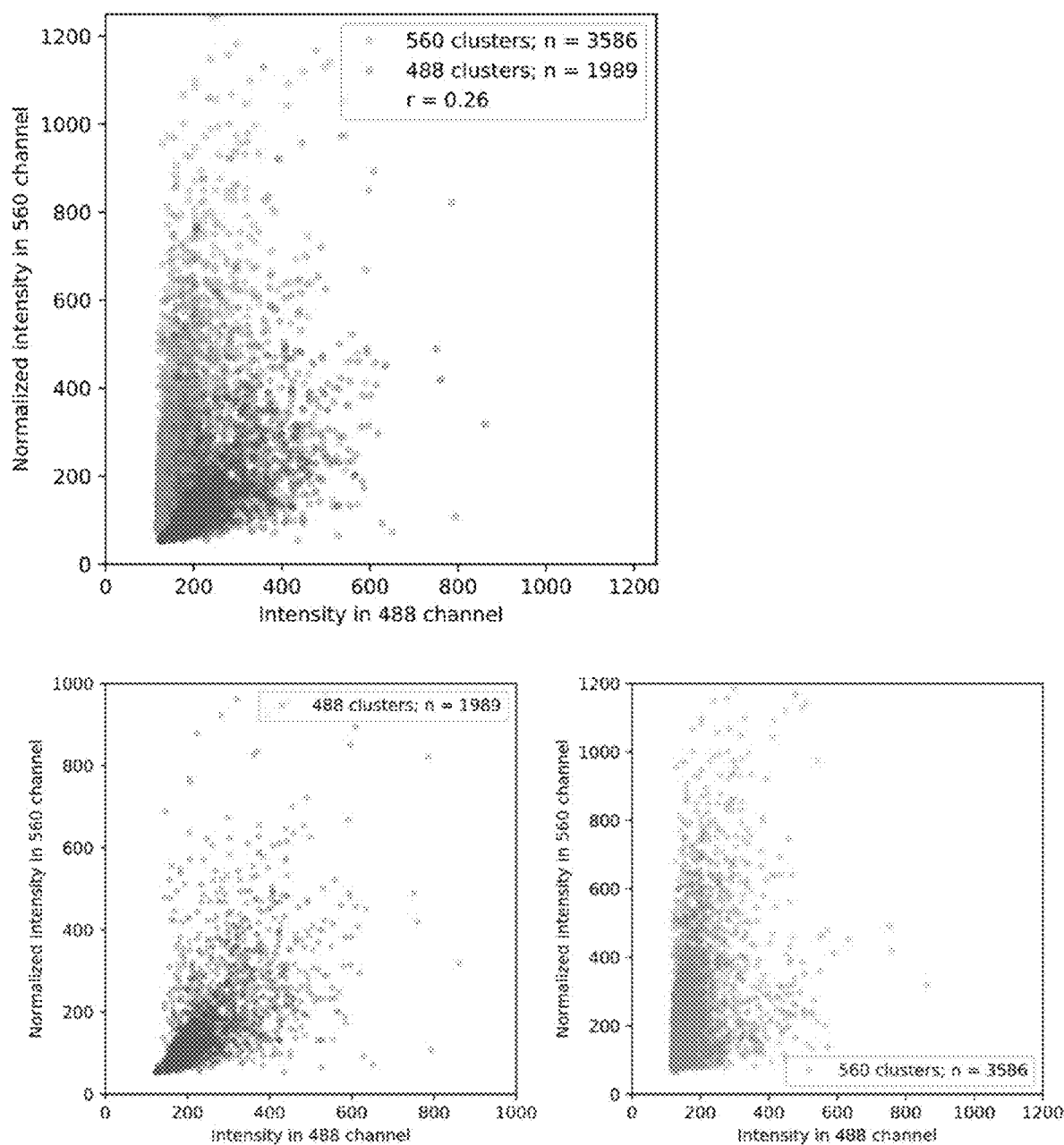
FIG. 12. Crosstalk plot for the seventh base of sequencing, with two rounds of synthesis before imaging. The two channels have not become significantly more correlated over seven cycles of sequencing.
Figure 13:
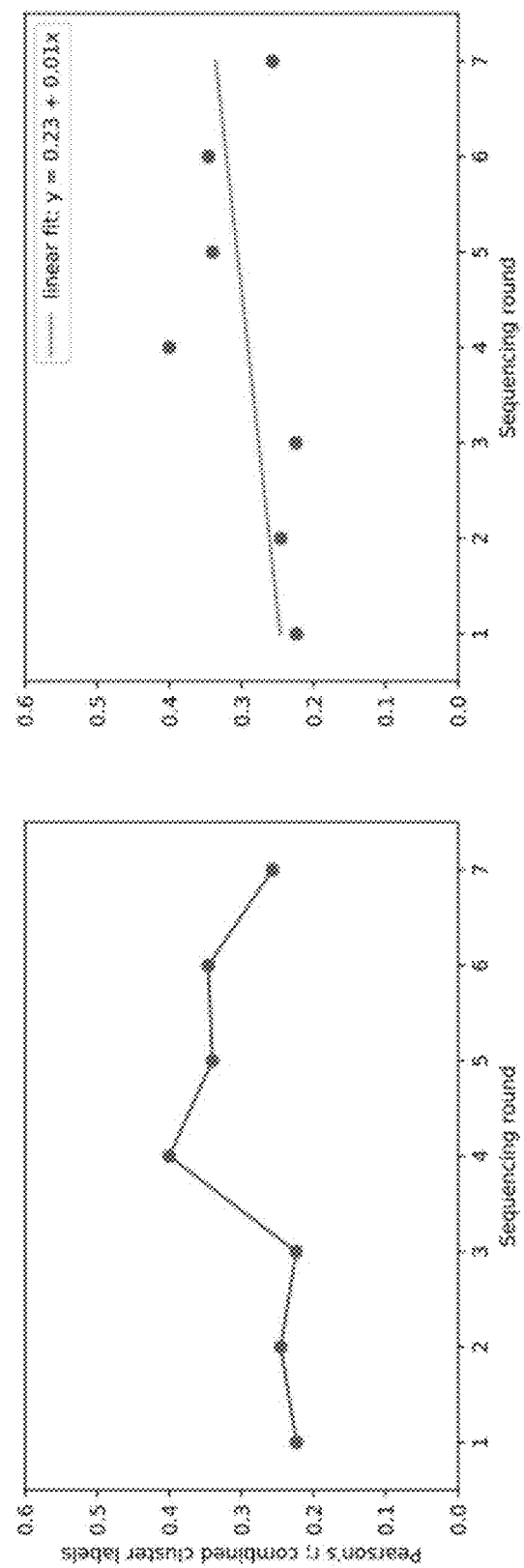
FIG. 13. Crosstalk plot correlation over multiple sequencing rounds with two rounds of synthesis.
Figure 14:
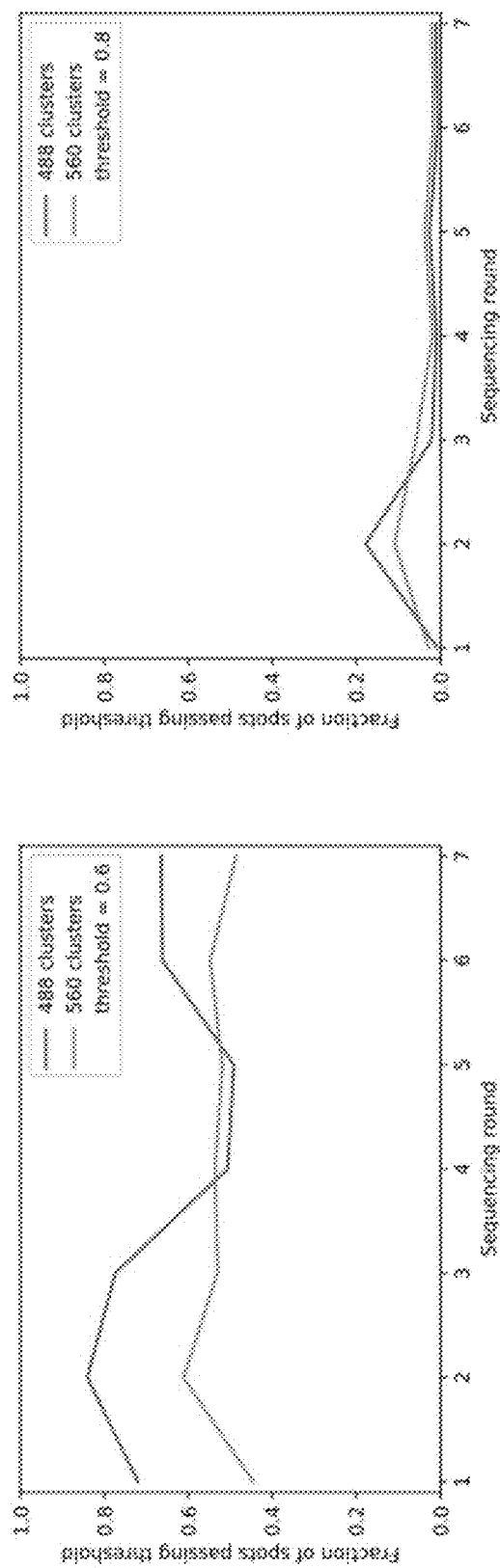
FIG. 14. Fraction of clusters passing the intensity threshold. Unlike the analogous case in FIG. 9, a significant fraction of clusters consistently pass the 0.6 threshold.
Figure 15:
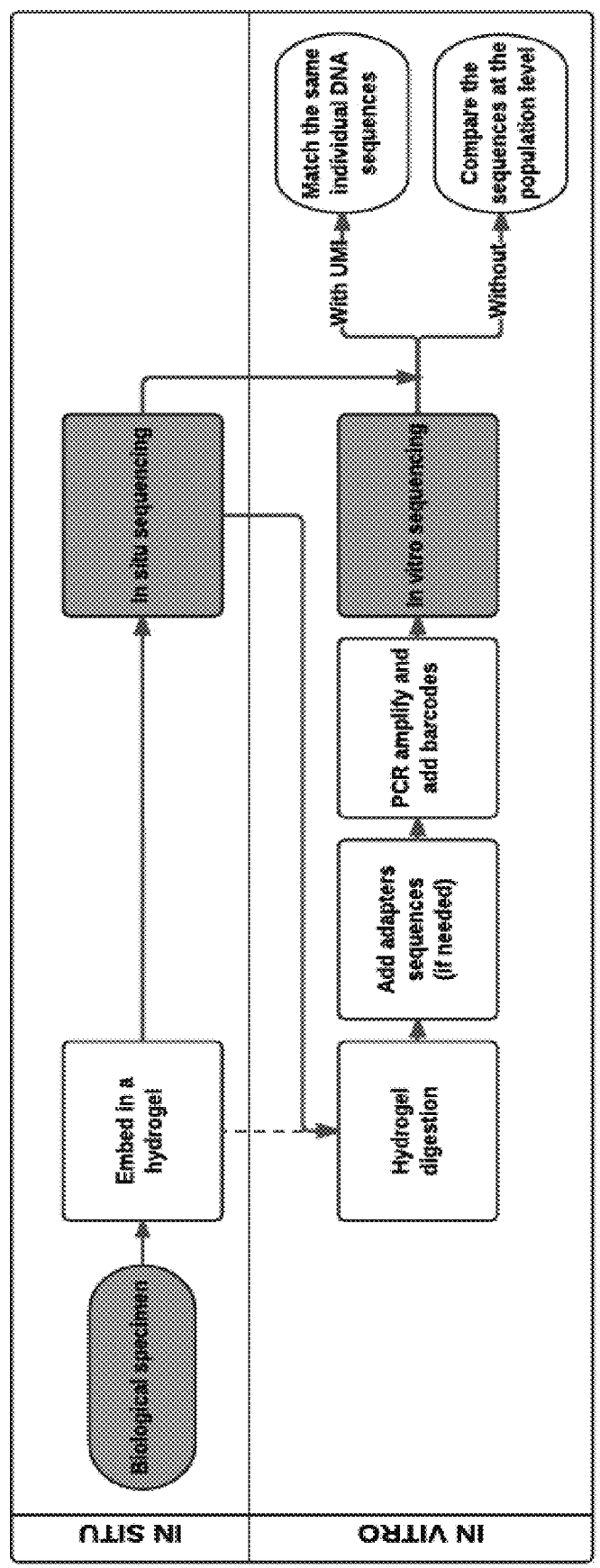
FIG. 15. A schematic illustrating workflow for augmenting in situ sequencing with in vitro sequencing information methods in accordance with the invention.

Seven cycles of imaging were performed, with two consecutive rounds of synthesis before each imaging cycle, on in situ RNA sequencing libraries prepared in hydrogel embedded and expanded rat neuron culture. Without wishing to be bound to any particular theory, it was hypothesized that multiple rounds of synthesis would increase dye addition efficiency and decrease phasing. A representative region of interest of a sample after the first imaging cycle is shown in FIG. 10. A crosstalk plot for the first base of sequencing is shown in FIG. 11. It was observed that the two components are not as well resolved as in the analogous case in Example Y: the two arms of the crosstalk plot have taken on a more conical shape as opposed to the sharply defined arms of FIG. 6, and the dataset is initially more correlated. However, after seven rounds of sequencing, as shown in FIG. 12, the crosstalk plot continues to maintain the same shape, and the correlation has not significantly increased. FIG. 13 shows that the correlation over all seven cycles of imaging is essentially constant. Similarly, FIG. 14 shows that the number of spots that pass an intensity threshold of 0.6 is also essentially constant over seven cycles of sequencing.

As described herein, in situ sequencing can be done in biological specimens that are fixed or embedded in a hydrogel. For example, the hydrogel can be, but not limited to, one of the following types:
  1) The monomer can be either acrylamide or sodium acrylate.
  2) The crosslinker can be either N,N'-methylenebis(acrylamide) (BIS) or N,N'-(1,2-dihydroxyethylene) bisacrylamide (DHEBA).
  3) The carboxylic groups of sodium acrylate can be passivated by covalently binding primary amines, as ethanolamine, to the carboxylic groups.
  4) Hydrogel can be re-embedded inside hydrogel, for example, acrylamide gel re-embedded inside sodium acrylate gel. These gels can contain the same type of crosslinker or a different type of crosslinker. For example, BIS crosslinker for the first hydrogel and DHEBA for the second one.
  5) Alternative acrylate gel recipes, varying in monomer and crosslinker, can be used.

After the biological specimen is embedded inside the hydrogel, DNA and RNA molecules can be targeted, converted to DNA molecules (if needed) and amplified in situ. In situ sequencing by ligation or by synthesis is then performed to identify the amplified DNA, and the DNA molecules are localized in 3D space. Note that before amplification the targeted DNA can be flanked with adapter sequences and/or with Unique Molecular Identifier (UMI). As described herein, the adapter sequences and UMI can later be used for in vitro sequencing.

To allow for in vitro sequencing, the embedded amplified DNA needs to be extracted. For samples which are not embedded in a hydrogel, standard DNA extraction methods can be used such as proteinase K and phenol chloroform extraction, or DNA purification columns. For samples within hydrogels, the hydrogels can be digested without damaging the embedded amplified DNA. For example, sodium periodate is known to digest acrylate gels that contain DHEBA crosslinker without damaging DNA and RNA molecules. Sodium acrylate gels, either passivated or not, can be digested with Periodate even without DHEBA crosslinker (see below). Different kinds of hydrogels, listed in the section above, can also be digested without damaging the amplified DNA with Periodate and/or by using other chemical or physical means. The DNA can be extracted and purified from the digested gel using DNA purification columns, Ethanol precipitation or other DNA purification methods.

If the extracted DNA is not flanked with adapter sequences, then the following steps can be used to prepare DNA for in vitro sequencing:
1) If the extracted DNA is single stranded, then it should be transformed into double strand DNA (dsDNA) with second strand cDNA synthesis. The DNA should then be purified as described above.
2) The Tn5 transposase should be used to simultaneously fragment and tag the dsDNA with adapter sequences required for the in vitro sequencing.

Alternative methods such as adapter ligation (see Illumina Truseq) can also be used to add adapters onto the extracted DNA.

The flanking adapter sequences can be used to PCR amplify the DNA with limited number of PCR cycles. To allow multiplexing during the high throughput in vitro sequencing, barcodes can be added during the PCR to uniquely mark individual samples.

The extracted DNA is now ready for high throughput sequencing in vitro. For example, by using Illumina sequencing. Other methods for high throughput sequencing can also be used. Note that the aforementioned adapter sequences and barcodes should correspond the chosen high throughput sequencing method.

Matching In Situ and In Vitro Sequencing Information
  Option 1: Matching the Same Individual DNA Sequences
  As the amplified DNA is sequenced both in situ and in vitro, it is possible make a direct correspondence between the two types of sequencing reads and therefore combine the spatial location of the in situ sequencing with the typically longer reads of in vitro sequencing. To match the two types of reads, a unique identifier needs to be present in both of them. One way to achieve this is by introducing a unique molecular identifier (UMI) to the amplified DNA. Then, by sequencing the DNA with the UMI in situ and also in vitro and by using sequence alignment techniques, it is possible to match the two types of reads.

Alternatively, an endogenous unique identifier can be used. For example, if random primers are used to reverse transcribe the mRNA, the resulting cDNA is expected to initiate at random locations inside the targeted mRNA, thereby allowing unique identification of the amplified cDNA. Similar to the UMI, the endogenous unique identifier can allow matching of the in situ and in vitro reads using sequence alignment techniques.

Option 2: Comparing the DNA Sequences at the Population Level
  Even if individual amplified DNA are not matched as described above, it is still possible to compare the amplified DNA at the population level. This comparison is informative for validation purposes, as it can reveal if the in situ data is in agreement with the more conventional, and widely used, in vitro sequencing. One method to compare the in situ and in vitro data is to align the sequences against common reference using sequence alignment techniques. For example, cDNA sequences generated in situ and in vitro can both be aligned against mRNA reference sequences, and the profile of alignment (that is, the number of times each reference sequence is read) can be compared between the two procedures.

Alternatively, the in vitro sequencing procedure can be performed even without the in situ sequencing procedure. This provides a fast way to characterize the amplified DNA inside the specimen, skipping the relatively slow step of in situ sequencing (albeit with the spatial information lost).

Sample Preparation

The biological specimen used was of the dentate gyrus region in the mouse brain. One adult mouse was anesthetized with isoflurane, decapitated, and the brain was frozen in OCT using dry ice in less than 5 minutes. The brain was cryosectioned and 14 um thick slice of the dentate gyrus region was selected. The slice was immediately fixed with 4% Formaldehyde in 1×PBS for 12 minutes, washed three times with 1×PBS, briefly treated (<2 minutes) with 4% Sodium dodecyl sulfate in 1×PBS, washed three times in 1×PBS, and then stored overnight in 70% ethanol @ 4° C.

In Situ Sequencing Inside a Hydrogel

The RNA molecules were bound in situ with the chemical reagent Label-X [LABEL IT®](Mirus Bio LLC), modified with the hydrogel anchorable group acryloyl-X], reacted with the slice overnight @ 37° C. The slice was then embedded inside acrylamide and sodium acrylate hydrogel. The RNA molecules were incorporated inside the forming gel due to the anchorable group of Label-X. The hydrogel was then expanded ~4 fold and re-embedded with acrylamide gel. The carboxylic groups of sodium acrylate were then passivated by binding ethanolamine to the carboxylic groups. Next, the endogenous DNA was digested with DNase I (0.5 U/µL; Roche) for 2 hours at room temperature.

The RNA molecules were reverse transcribed to cDNA with random primers, the RNA was digested, the cDNA circularized and amplified with rolling circle amplification. In situ sequencing by ligation was then performed on the sample resulting with 20 bases long reads.

Hydrogel Digestion, DNA Extraction, and Preparing the DNA for In Vitro Sequencing The hydrogel was digested with 20 mM sodium metaperiodate in 1×PBS pH 6 @ 37 C for 12 hours, followed by vortexing. Different concentrations of Periodate, buffer conditions, incubation temperatures and duration can be used to digest the hydrogel without damaging the DNA.

The DNA was extracted and purified from the digested hydrogel with Genomic DNA Clean & Concentrator Kit (Zymo Research), and then the single stranded DNA was transformed into dsDNA with NEBNext (New England Biolabs). Nextera XT DNA Library Preparation Kit (Illumina) was used to simultaneously fragment and tag the dsDNA with the adapter sequences required for the illumina MiSeq in vitro sequencing. Nextera XT Index Kit (Illumina) was used to add Illumina sequencing barcodes during the PCR amplification of the extracted DNA.

In Vitro Sequencing and Matching to In Situ Sequencing Data

MiSeq instrument was used to sequence the extracted DNA with MiSeq® Reagent Kit v3 (600 cycles; illumina). As random primers were used to reverse transcribe the mRNA, the resulting cDNA initiated at random locations inside the targeted mRNA, thereby allowing unique identification of the amplified cDNA. The alignment tool Blast was used to align the individual in situ sequencing reads to the Illumina in vitro sequencing reads (see FIG. 16).

Figure 16:
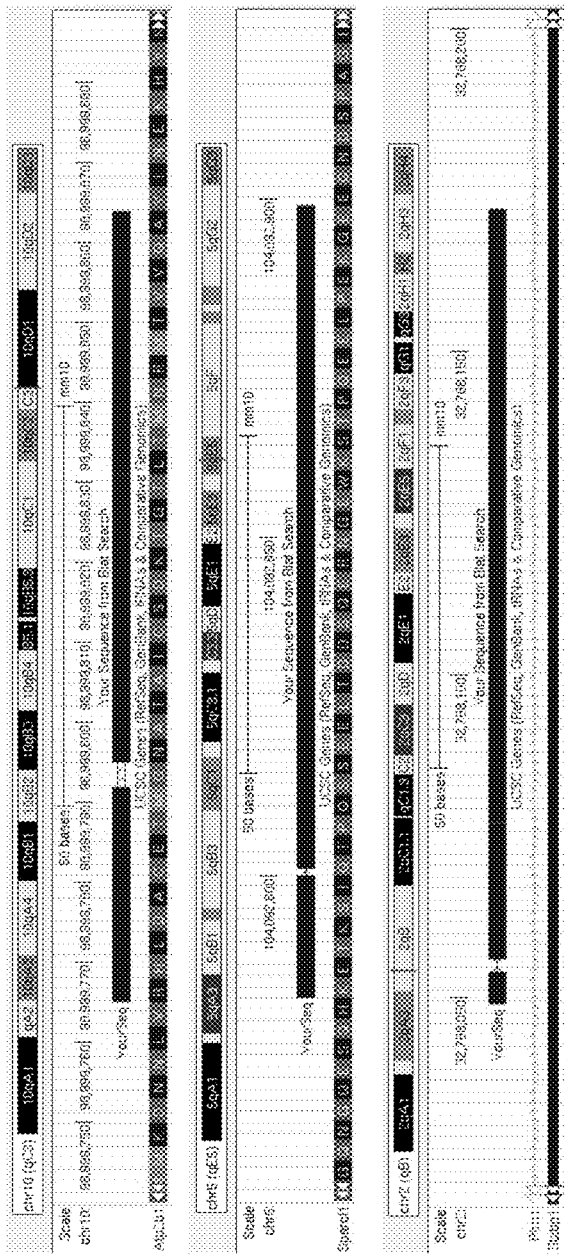
FIG. 16. Demonstrating that the in vitro sequencing information is augmenting the in situ information.

FIG. 16 shows that the in vitro sequencing information is augmenting the in situ information. Three examples of individual in situ sequencing reads that were matched to the Illumina in vitro sequencing reads. The in vitro sequences (black ribbons) are aligned against the mouse genome using the UCSC genome browser BLAT tool. The first two sequences are aligned against the coding regions of the genes Atp2b1 and Sparcl1, respectively, whereas the third is aligned against the non-coding region of the gene Stxbp1. The in situ sequences shown (red box) are 17 bases long on average whereas the in vitro sequences are 113 bases long on average.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the preferred embodiments described herein are not mutually exclusive and that features from the various preferred embodiments may be combined in whole or in part in accordance with the invention.

What is claimed is:

1. A method for in-situ sequencing of target nucleic acids present in a biological sample comprising the steps of:
    (a) permeating the sample with a composition comprising precursors of a swellable material;
    (b) initiating polymerization to form a swellable material, wherein the swellable material is bound to the small molecule linker or a nucleic acid adaptor to form a sample-swellable material complex;
    (c) adding an aqueous solvent or liquid to cause the sample-swellable material complex to swell, thereby physically expanding the complex to form an enlarged sample;
    (d) modifying the target nucleic acids or the nucleic acid adaptor to form a nucleic acid adaptor useful for sequencing;
    (e) in situ sequencing of the nucleic acids in the enlarged sample;
    (f) digesting the sample:
    (g) isolating the nucleic acids from the digested sample; and
    (h) in vitro sequencing of the nucleic acids.

2. The method of claim 1, wherein prior to or after step (a) the sample is contacted with a small molecule linker or a nucleic acid adaptor comprising a binding moiety and an anchor, wherein the binding moiety binds to target nucleic acids in the sample; and wherein the anchor comprises a polymerizable moiety.

3. The method of claim 1, wherein prior to or after step (d) the enlarged sample is re-embedded in a non-swellable polymer gel.

4. The method of claim 1, wherein modifying the target nucleic acids or the nucleic acid adapter comprises contacting the target nucleic acids or the nucleic acid adapter with reverse transcriptase.

5. The method of claim 1, wherein the sequencing step of step (e) is fluorescence in situ sequencing.

6. The method of claim 1, further comprising repeating steps a) through c) on the enlarged sample to further enlarge the sample prior to in situ sequencing.

7. The method of claim 1, wherein nucleic acid adaptors are linked to target nucleic acids via ligation to the target nucleic acid.

8. The method of claim 1, wherein the small molecule linkers are attached to target nucleic acids via a chemical reactive group capable of covalently binding the target nucleic acid.

9. The method of claim 3, further comprising the step of passivating the swellable material after re-embedding the enlarged sample in a non-swellable material.

10. The method of claim 1, wherein prior to step (a), the sample is treated with a detergent.

11. The method of claim 1, wherein prior to step (c) the sample is subjected to a disruption of the endogenous physical structure of the sample.

12. The method of claim 11, wherein the digestion disruption is a physical, chemical, or enzymatic disruption of the sample.

13. The method of claim 1, wherein the aqueous solvent or liquid is water.

14. The method of claim 1, wherein the swellable material is a hydrogel.

15. The method according to claim 14, wherein the hydrogel is a polyacrylate hydrogel.

16. The method of claim 1, wherein the nucleic acid is DNA.

17. The method of claim 1, wherein the nucleic acid is RNA.

18. The method of claim 1, wherein prior to step (g), the isolated nucleic acids are amplified.

19. The method of claim 18, wherein the isolated nucleic acids are amplified by PCR.

20. The method of claim 18, wherein barcodes are added to the isolated nucleic acids during amplification.

21. The method according to claim 1, wherein the sample is expanded isotropically by adding an aqueous solvent or liquid to swell the swellable material.

* * * * *

UNITED STATES PATENT AND TRADEMARK OFFICE
CERTIFICATE OF CORRECTION

PATENT NO. : 10,526,649 B2
APPLICATION NO. : 15/789419
DATED : January 7, 2020
INVENTOR(S) : Chen et al.

It is certified that error appears in the above-identified patent and that said Letters Patent is hereby corrected as shown below:

In the Specification

In Column 1, Lines 15-22, delete:
"This invention was made with Government support under grant numbers 2389114 Life Sciences Research Foundation 3843505, discretionary 6933228, Harvard University 6927725, ML Consortia 6930094, RIC 6934416, HMS 6927725, ML Consortia 6934733, NIH 6929218, NIH 6932279, NIH 6926636, NIH 6928057, ML Consortia 6934493, U-Mich 6935966, Cancer Research UK. The government has certain rights in the invention."

And insert:
-- This invention was made with government support under HG005550, HG008525, R01 MH008525, and R01 MH103910 awarded by the National Institutes of Health, W911NF-15-1-0548 awarded by the U.S. Army Research Office, and DGE1144152 awarded by the National Science Foundation. The government has certain rights in the invention. --

Signed and Sealed this
Ninth Day of December, 2025

John A. Squires
*Director of the United States Patent and Trademark Office*

SEQUENCE LISTING

```
<160> NUMBER OF SEQ ID NOS: 5

<210> SEQ ID NO 1
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 1
gtactgaact gtctcttata cacatctgac gctgccgacg a                41

<210> SEQ ID NO 2
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 2
gtactgttct gtctcttata cacatctgac gctgccgacg a                41

<210> SEQ ID NO 3
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 3
gtactgccct gtctcttata cacatctgac gctgccgacg a                41

<210> SEQ ID NO 4
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 4
gtactgggct gtctcttata cacatctgac gctgccgacg a                41

<210> SEQ ID NO 5
<211> LENGTH: 33
<212> TYPE: DNA
<213> ORGANISM: Artificial Sequence
```

```
<220> FEATURE:
<223> OTHER INFORMATION: Synthetic oligonucleotide

<400> SEQUENCE: 5
tcgtcggcag cgtcagatgt gtataagaga cag                               33
```